US012614275B2

(12) United States Patent
Zhang

(10) Patent No.: US 12,614,275 B2
(45) Date of Patent: Apr. 28, 2026

(54) SYSTEM AND METHOD FOR HYBRID IMAGING

(71) Applicant: SHANGHAI UNITED IMAGING HEALTHCARE CO., LTD., Shanghai (CN)

(72) Inventor: Zheng Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 517 days.

(21) Appl. No.: 17/815,565

(22) Filed: Jul. 27, 2022

(65) Prior Publication Data

US 2023/0045406 A1    Feb. 9, 2023

(30) Foreign Application Priority Data

Aug. 6, 2021    (CN) .......................... 202110901563.8

(51) Int. Cl.
*G06T 7/00*        (2017.01)
*A61B 5/00*        (2006.01)
(Continued)

(52) U.S. Cl.
CPC ............ *G06T 7/0012* (2013.01); *A61B 5/055* (2013.01); *A61B 5/7292* (2013.01); *A61B 6/037* (2013.01);
(Continued)

(58) Field of Classification Search
CPC ....... G06T 7/0012; G06T 7/33; G06T 11/005; G06T 11/008; G06T 2207/10081;
(Continued)

(56) References Cited

U.S. PATENT DOCUMENTS 6,741,880 B1 *    5/2004    Foo ........................ G01R 33/54
                                                        600/407
7,945,305 B2 *    5/2011    Aggarwal .......... G01R 33/5673
                                                        600/407
(Continued)

FOREIGN PATENT DOCUMENTS

CN        107977926 A        5/2018
CN        108053428 A        5/2018
CN        109961419 A        7/2019

OTHER PUBLICATIONS

Russo, V., Lovato, L. & Ligabue, G. Cardiac MRI: technical basis. Radiol med 125, 1040-1055 (2020). https://doi.org/10.1007/s11547-020-01282-z (Year: 2020).*

(Continued)

*Primary Examiner* — Chineyere Wills-Burns
*Assistant Examiner* — Lucius Cameron Gree Allen
(74) *Attorney, Agent, or Firm* — METIS IP LLC

(57) ABSTRACT

The present disclosure provides systems and methods for hybrid imaging. The systems and methods may obtain a first magnetic resonance (MR) image of a target object. The first MR image may be acquired by a magnetic resonance imaging (MRI) device using a first imaging sequence. The systems and methods may also obtain a second MR image of the target object. The second MR image may be acquired by the MRI device using a second imaging sequence. The second MR image may correspond to a target respiratory phase of the target object. The systems and methods may also obtain a target emission computed tomography ECT) image of the target object. The target ECT image may correspond to the target respiratory phase. The systems and methods may further fuse, based on the second MR image, the first MR image and the target ECT image.

18 Claims, 10 Drawing Sheets

(51) Int. Cl.

| | |
|---|---|
| *A61B 5/055* | (2006.01) |
| *A61B 6/00* | (2024.01) |
| *A61B 6/03* | (2006.01) |
| *A61B 6/50* | (2024.01) |
| *G01R 33/48* | (2006.01) |
| *G01R 33/565* | (2006.01) |
| *G06T 5/50* | (2006.01) |
| *G06T 7/33* | (2017.01) |
| *G06T 11/00* | (2006.01) |

(52) U.S. Cl.
CPC .............. *G01R 33/481* (2013.01); *G06T 7/33* (2017.01); *G06T 11/005* (2013.01); *G06T 11/008* (2013.01); *G06T 2207/10081* (2013.01); *G06T 2207/10084* (2013.01); *G06T 2207/10088* (2013.01); *G06T 2207/20221* (2013.01); *G06T 2207/30048* (2013.01); *G06T 2211/408* (2013.01)

(58) Field of Classification Search
CPC . G06T 2207/10084; G06T 2207/10088; G06T 2207/20221; G06T 2207/30048; G06T 2211/408; G06T 5/50; A61B 5/055; A61B 5/7292; A61B 6/037; A61B 6/5288; A61B 6/4417; A61B 6/503; A61B 6/5247; G01R 33/481; G01R 33/56509
USPC ......................................................... 382/131
See application file for complete search history.

(56) References Cited

U.S. PATENT DOCUMENTS

| | | | | | |
|---|---|---|---|---|---|
| 8,606,045 | B2* | 12/2013 | Lee | ...................... | A61B 8/4416 |
| | | | | | 600/407 |
| 9,495,771 | B2* | 11/2016 | El Fakhri | .............. | A61B 6/5264 |
| 2008/0298664 | A1* | 12/2008 | Martin | ................... | G16H 30/20 |
| | | | | | 382/131 |
| 2013/0101193 | A1* | 4/2013 | Ra | ......................... | G06T 11/005 |
| | | | | | 382/131 |
| 2013/0106414 | A1* | 5/2013 | Schmidt | ............... | A61B 5/7292 |
| | | | | | 324/309 |
| 2013/0195341 | A1* | 8/2013 | Liu | ....................... | G06T 11/005 |
| | | | | | 382/131 |
| 2014/0355855 | A1 | 12/2014 | Miao et al. | | |
| 2014/0357980 | A1* | 12/2014 | Hayes | .................... | A61B 6/037 |
| | | | | | 600/411 |

| | | | | | |
|---|---|---|---|---|---|
| 2016/0098833 | A1* | 4/2016 | Tsadok | ................... | G06V 10/46 |
| | | | | | 382/128 |
| 2016/0116614 | A1* | 4/2016 | Watson | ................ | A61B 6/4429 |
| | | | | | 250/363.03 |
| 2016/0125605 | A1* | 5/2016 | Lee | ........................ | A61B 6/541 |
| | | | | | 382/131 |
| 2018/0314906 | A1* | 11/2018 | Yang | .................... | G06V 10/462 |
| 2019/0064292 | A1* | 2/2019 | Leghissa | ............ | G01R 33/5608 |
| 2019/0101655 | A1* | 4/2019 | Wang | .................... | G01R 33/28 |
| 2019/0236816 | A1* | 8/2019 | Wang | .................... | A61B 6/037 |
| 2019/0302211 | A1* | 10/2019 | Cai | ........................... | G06T 7/20 |
| 2019/0347790 | A1* | 11/2019 | Lee | ..................... | A61B 5/0075 |
| 2020/0098120 | A1* | 3/2020 | Tang | ..................... | A61B 8/5207 |
| 2020/0151919 | A1* | 5/2020 | Benkert | .............. | G01R 33/565 |
| 2021/0012546 | A1* | 1/2021 | Wieczorek | ........... | G06T 11/008 |
| 2022/0101576 | A1* | 3/2022 | Kaushik | ............... | G06T 11/006 |

OTHER PUBLICATIONS

Polycarpou, Irene et al. "Synergistic motion compensation strategies for positron emission tomography when acquired simultaneously with magnetic resonance imaging." Philosophical transactions. Series A, Mathematical, physical, and engineering sciences vol. 379,2204 (2021): Feb. 7, 2020 (Year: 2021).*

Costa Daniel N. et al. "Body MRI Using Ideal" American Journal of Roentgenology vol. 190, Issue 4 (2008), Apr. 2008 (Year: 2008).*

Kolbitsch C, Ahlman MA, Davies-Venn C, Evers R, Hansen M, Peressutti D, Marsden P, Kellman P, Bluemke DA, Schaeffter T. Cardiac and Respiratory Motion Correction for Simultaneous Cardiac PET/MR. J Nucl Med. May 2017; (Year: 2017).*

Zhang, Zheng et al., A Two-Stage Cardiac PET and Late Gadolinium Enhancement MRI Co-Registration Method for Improved Assessment of Non-Ischemic Cardiomyopathies Using Integrated PET/MR, European Journal of Nuclear Medicine and Molecular Imaging, 49: 2199-2208, 2022.

Carmela Nappi et al., State of the Art in Cardiac Hybrid Technology: PET/MR, Current Cardiovascular Imaging Reports, 6(4): 338-345, 2013.

Pawel J. Markiewicz et al., Uncertainty Analysis of MR-PET Image Registration for Precision Neuro-PET Imaging, NeuroImage, 2021, 9 pages.

Pan, Xiaoguang, Medical Image Registration and Application, Doctoral Dissertation of Northeastern University, 2017, 137 pages.

First Office Action in Chinese Application No. 202110901563.8 mailed on Nov. 11, 2025, 20 pages.

* cited by examiner

100

200

Processor
210

Storage Device
220

I/O
230

Communication
Port
240

300

Communication Platform
310

Display
320

GPU
330

OS
370

CPU
340

App(s)
380

Memory   360

I/O
350

Storage
390

120

Obtaining Module   402

Attenuation Correction Module   404

Fusion Module   406

Reconstruction Module   408

<u>500</u>

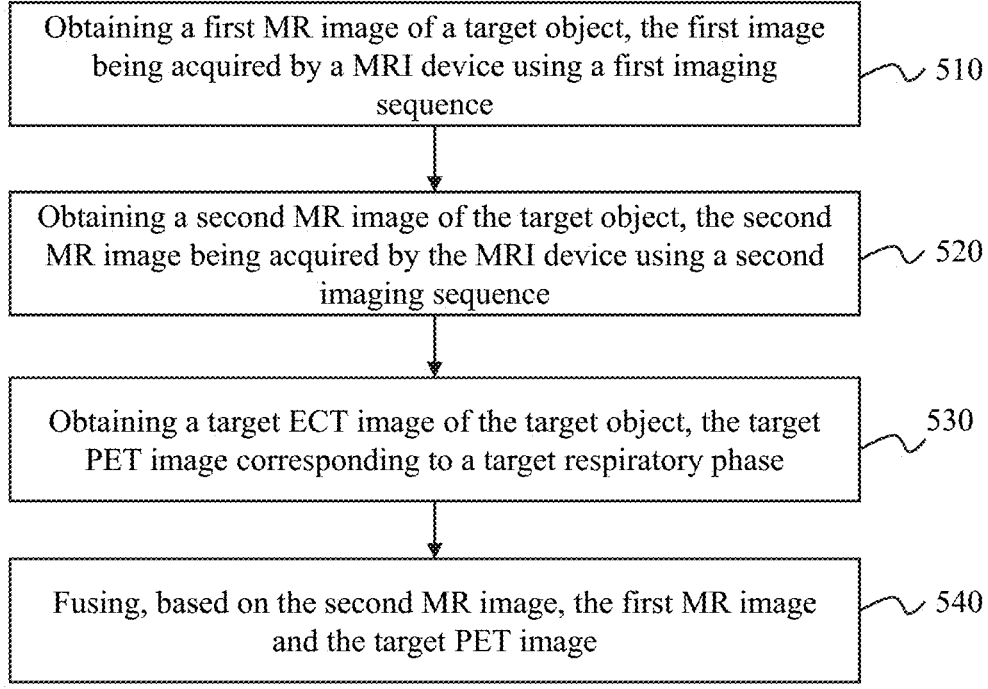

| Obtaining a first MR image of a target object, the first image being acquired by a MRI device using a first imaging sequence |
510

↓

| Obtaining a second MR image of the target object, the second MR image being acquired by the MRI device using a second imaging sequence |
520

↓

| Obtaining a target ECT image of the target object, the target PET image corresponding to a target respiratory phase |
530

↓

| Fusing, based on the second MR image, the first MR image and the target PET image |
540

Obtaining PET data of the target object acquired when the target object is breathing freely ~ 610

Obtaining an attenuation map determined based on the second MR image of the target object ~ 620

Determining a target PET image of the target object based on the PET data of the target object and the attenuation map ~ 630

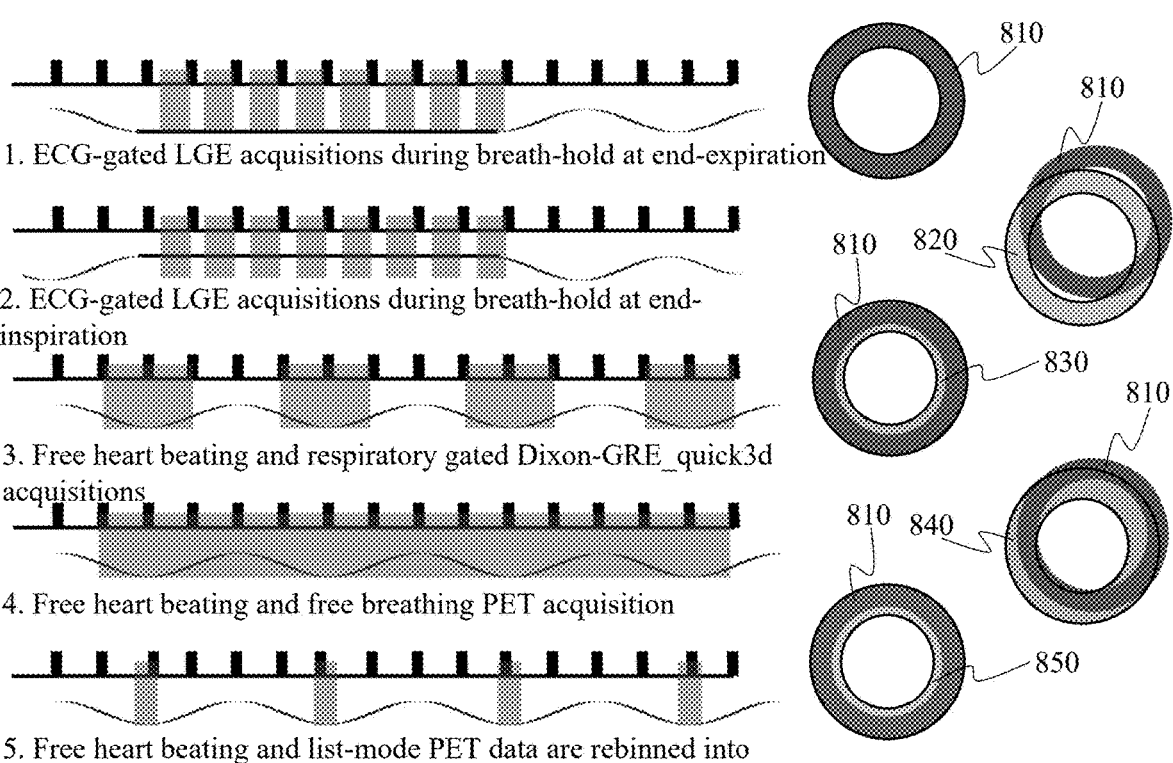

1. ECG-gated LGE acquisitions during breath-hold at end-expiration

2. ECG-gated LGE acquisitions during breath-hold at end-inspiration

3. Free heart beating and respiratory gated Dixon-GRE_quick3d acquisitions

4. Free heart beating and free breathing PET acquisition

5. Free heart beating and list-mode PET data are rebinned into respiratory gated sinograms for reconstruction

FIG. 8

910 — PET IMAGE average

RESPIRATORY GATED RECON 920-1 — PET IMAGE Phase 1

920-2 — PET IMAGE Phase 2

930-3 — PET IMAGE Phase 3

........

910-m — PET IMAGE Phase m

........

PET IMAGE Phase n

940 — MR IMAGE Quick3d_dixon Respiratory Gated Acquisition

REGISTRATION MR - MR 950-1 — MR IMAGE fse dark blood

950-2 — MR IMAGE cine

950-3 — MR IMAGE perfusion

950-4 — MR IMAGE LGE

950-5 — MR IMAGE mapping

950-6 — MR IMAGE flow

........

960 — Breath Hold & ECG Gated

FIG. 9

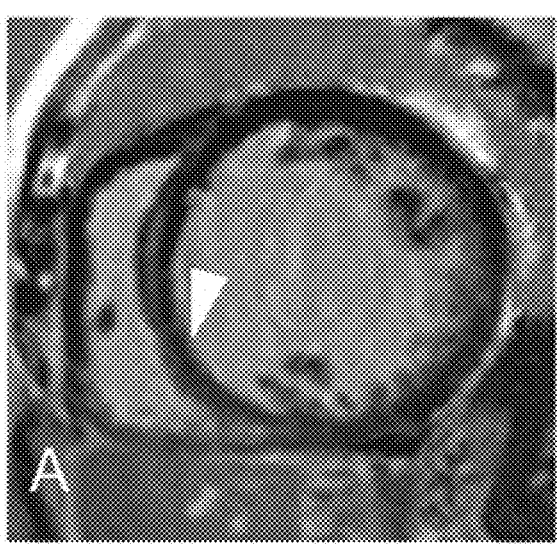
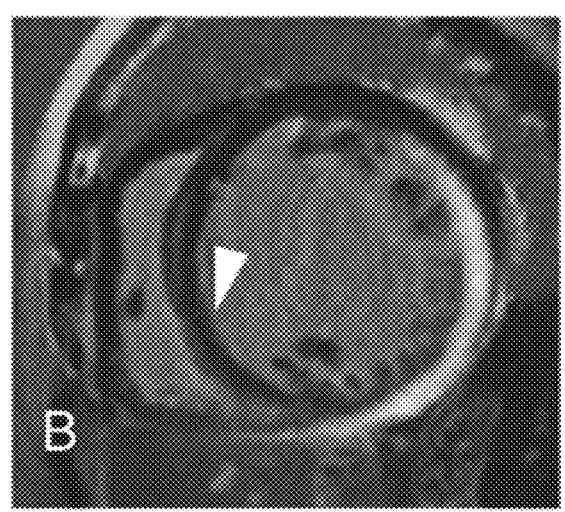
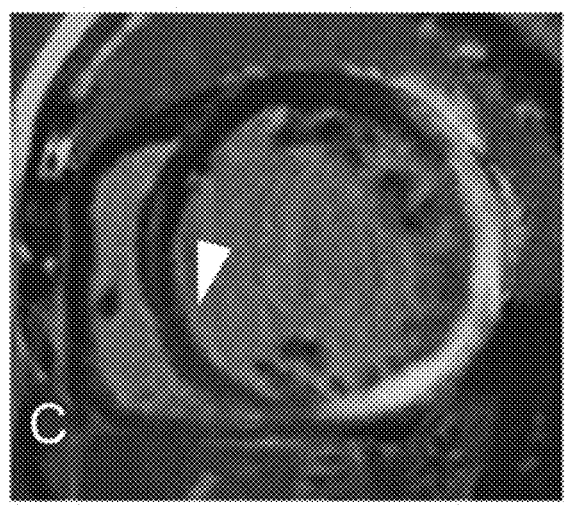
FIG. 12

<u>1300</u>

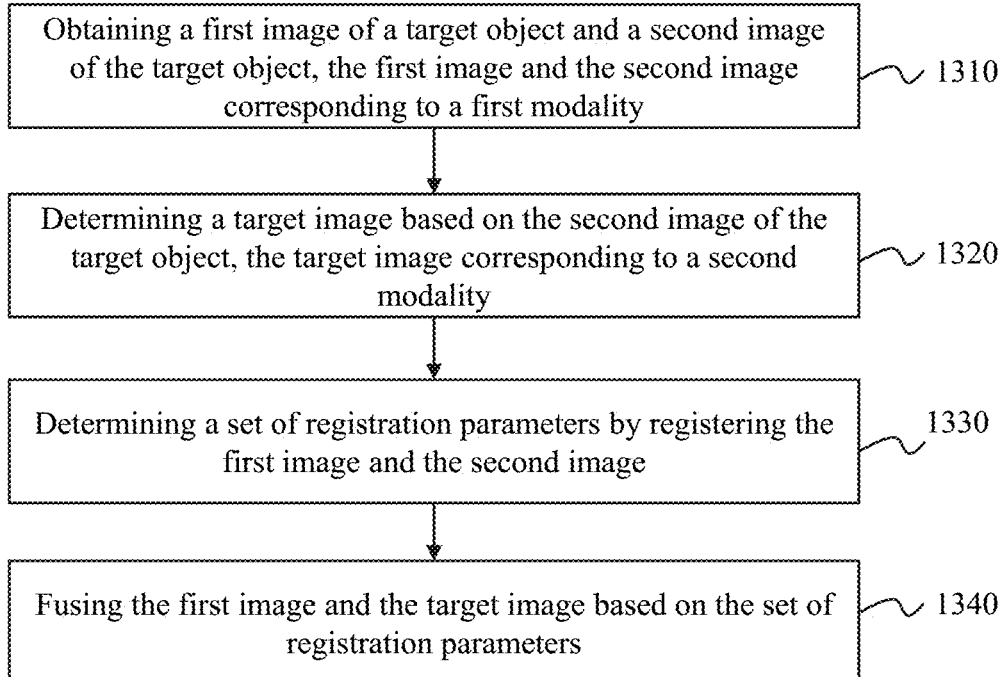

Obtaining a first image of a target object and a second image
of the target object, the first image and the second image
corresponding to a first modality                            1310

Determining a target image based on the second image of the
target object, the target image corresponding to a second
modality                                                      1320

Determining a set of registration parameters by registering the
first image and the second image                             1330

Fusing the first image and the target image based on the set of
registration parameters                                      1340

FIG. 13

SYSTEM AND METHOD FOR HYBRID IMAGING

CROSS-REFERENCE TO RELATED APPLICATIONS

This application claims priority of Chinese Application No. 202110901563.8 filed on Aug. 6, 2021, the contents of which are hereby incorporated by reference.

TECHNICAL FIELD

This disclosure generally relates to the image fusion technology, and more particularly, relates to systems and methods for hybrid imaging.

BACKGROUND

Positron emission tomography-magnetic resonance imaging (PET-MRI) system is a molecular and structural medical system that combines PET technology and MRI technology. With the high resolution of MRI and the high sensitivity of PET, anatomical imaging and functional imaging can be complementary, achieving the combination and cross-validation of the anatomical imaging and the functional imaging, which in turn may facilitate the diagnosis and/or monitoring of some complex diseases.

During an imaging (e.g., cardiac imaging) process using the PET-MRI system, involuntary motions (e.g., respiratory motion, cardiac motion) may cause a mismatch between PET image(s) and MR image(s) acquired during the imaging process. The mismatch may affect the attenuation correction of the PET image(s) and/or fusion of the PET image(s) and the MR image(s), resulting in low image quality of the PET image(s) and/or a fusion image of the PET image(s) and the MR image(s). Therefore, it is desirable to provide a system and method for hybrid imaging (e.g., the PET-MR imaging), thereby improving the image quality of the PET image(s) and/or fusion image of the PET image(s) and the MR image(s), which in turn can improve the accuracy of diagnosis performed based on the PET image(s) and/or fusion image.

SUMMARY

In an aspect of the present disclosure, a system for hybrid imaging is provided. The system may include at least one storage device including a set of instructions and at least one processor configured to communicate with the at least one storage device. When executing the set of instructions, the at least one processor may be configured to direct the system to perform the following operations. The operations may include obtaining a first magnetic resonance (MR) image of a target object. The first MR image may be acquired by a magnetic resonance imaging (MRI) device using a first imaging sequence. The operations may also include obtaining a second MR image of the target object. The second MR image may be acquired by the MRI device using a second imaging sequence. The second MR image may correspond to a target respiratory phase of the target object. The operations may also include obtaining a target emission computed tomography (ECT) image of the target object. The target ECT image may correspond to the target respiratory phase. The operations may further include fusing, based on the second MR image, the first MR image and the target ECT image.

In some embodiments, the first MR image may be acquired with cardiac gating during a breath-hold period of the target object.

In some embodiments, the target respiratory phase may include an end-expiratory phase of a respiratory cycle.

In some embodiments, the second MR image may be acquired when the target object is breathing freely.

In some embodiments, the second MR image and the target ECT image may correspond to a same coordinate system.

In some embodiments, the obtaining a target PET image of the target object may include obtaining ECT data of the target object acquired when the target object is breathing freely; obtaining an attenuation map determined based on the second MR image of the target object; and determining the target ECT image of the target object based on the ECT data of the target object and the attenuation map.

In some embodiments, the determining the target ECT image of the target object based on the ECT data of the target object and the attenuation map may include generating corrected ECT data by correcting, based on the attenuation map, the ECT data of the target object; generating, based on the corrected ECT data, a plurality of candidate ECT images; and determining, based on the target respiratory phase, the target ECT image of the target object from the plurality of candidate ECT images. Each of the plurality of candidate ECT images may correspond to a respiratory phase of a respiratory cycle.

In some embodiments, the determining the target ECT image of the target object based on the ECT data of the target object and the attenuation map may include determining a set of target ECT sub-data from the ECT data of the target object; generating a set of corrected target ECT sub-data by correcting, based on the attenuation map, the set of target ECT sub-data; and generating, based on the set of corrected target ECT sub-data, the target PET image of the target object. The set of target ECT sub-data may correspond to the target respiratory phase In some embodiments, the fusing, based on the second MR image, the first MR image and the target ECT image may include determining a set of registration parameters by registering the first MR image and the second MR image; and fusing, based on the set of registration parameters, the first MR image and the target ECT image.

In some embodiments, the determining the set of registration parameters may include obtaining, in a three-dimensional space, translational degrees of freedom, rotational degrees of freedom, and telescopic degrees of freedom of the first MR image; and determining the set of registration parameters by registering, according to the translational degrees of freedom, the rotational degrees of freedom, and the telescopic degrees, the first MR image and the second MR image using a generalized pattern search (GPS) algorithm.

In some embodiments, the target object may include the heart of a patient, a lung of the patient, or the liver of the patient.

In some embodiments, the first imaging sequence may include at least one of a fse dark blood sequence, a cine sequence, a perfusion sequence, a late gadolinium enhancement (LGE) sequence, a mapping sequence, or a low sequence.

In some embodiments, the second imaging sequence may be related to a two-point Dixon technique or an iterative decomposition of water and fat with echo asymmetric and least-squares estimation technique.

In some embodiments, the first MR image may include a 2D image or a 3D image, and the second MR image may include a 3D image.

In another aspect of the present disclosure, a method for hybrid imaging is provided. The method may be implemented on a computing device including at least storage device and at least processor. The method may include obtaining a first magnetic resonance (MR) image of a target object. The first MR image may be acquired by a magnetic resonance imaging (MRI) device using a first imaging sequence. The method may also include obtaining a second MR image of the target object. The second MR image may be acquired by the MRI device using a second imaging sequence with respiratory gating. The second MR image may correspond to a target respiratory phase of the target object. The method may also include obtaining a target emission computed tomography (ECT) image of the target object. The target ECT image may correspond to the target respiratory phase. The method may further include fusing, based on the second MR image, the first MR image and the target ECT image.

In another aspect of the present disclosure, a system for hybrid imaging is provided. The system may include at least one storage device including a set of instructions and at least one processor configured to communicate with the at least one storage device. When executing the set of instructions, the at least one processor may be configured to direct the system to perform following operations. The operations may include obtaining a first image of a target object and a second image of the target object; determining a target image based on the second image of the target object; determining a set of registration parameters by registering the first image and the second image; and fusing the first image and the target image based on the first set of registration parameters. The first image and the second image may correspond to a first modality. The target image may correspond to a second modality.

In some embodiments, the first modality may be magnetic resonance imaging (MRI), and the second modality may be emission computed tomography (ECT).

In some embodiments, the first image may be a first magnetic resonance (MR) image that is acquired by a magnetic resonance imaging (MRI) device using a first imaging sequence during a breath-hold period of the target object, the second image may be a second MR image that is acquired by the MRI device using a second imaging sequence when the target object is breathing freely.

In some embodiments, the determining a target image based on the second image of the target object may include obtaining ECT data of the target object acquired when the target object is breathing freely; obtaining an attenuation map determined based on the second image of the target object; and determining the target ECT image of the target object based on the ECT data of the target object and the attenuation map.

In some embodiments, the second image and the target image may correspond to a target respiratory phase.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

4

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for image fusion according to some embodiments of the present disclosure;

FIG. 8 is a schematic diagram illustrating different exemplary imaging manners according to some embodiments of the present disclosure;

FIG. 9 is a schematic diagram illustrating an exemplary process for image registration according to some embodiments of the present disclosure;

FIG. 12 illustrates exemplary images according to some embodiments of the present disclosure; and FIG. 13 is a flowchart illustrating an exemplary process for image fusion according to some embodiments of the present disclosure.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
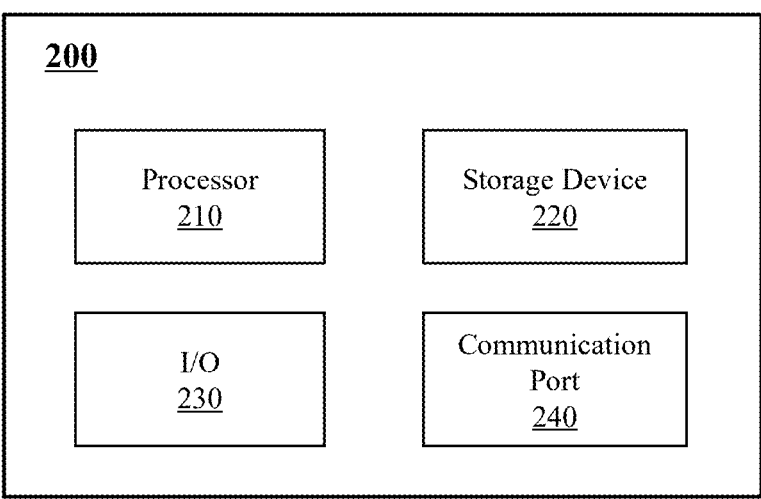
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second,"

and "third," etc., are used to distinguish similar objects and do not represent a specific order of the objects.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood that the operations of the flowchart may be implemented not in order. Conversely, the operations may be implemented in inverted order, or simultaneously. Moreover, one or more other operations may be added to the flowcharts. One or more operations may be removed from the flowcharts.

In the present disclosure, the term "image" may refer to a two-dimensional (2D) image, a three-dimensional (3D) image, or a four-dimensional (4D) image. In some embodiments, the term "image" may refer to an image of a region (e.g., a region of interest (ROI)) of a subject. As described above, the image may be a PET image, an MR image, a PET-MR fusion image, etc. As used herein, the term "attenuation correction" relating to a PET image may refer to that a photon may be scattered or absorbed by tissue in a medium when the photon traverses the medium, and the attenuation due to such scattering or absorption may need to be compensated in order to obtain a PET image of sufficient quality for quantitative analysis.

As used herein, a representation of a subject (e.g., a patient, or a portion thereof) in an image may be referred to as the subject for brevity. For instance, a representation of an organ or tissue (e.g., the heart, the liver, a lung, etc., of a patient) in an image may be referred to as the organ or tissue for brevity. An image including a representation of a subject may be referred to as an image of the subject or an image including the subject for brevity. As used herein, an operation on a representation of a subject in an image may be referred to as an operation on the subject for brevity. For instance, a segmentation of a portion of an image including a representation of an organ or tissue (e.g., the heart, the liver, a lung, etc., of a patient) from the image may be referred to as a segmentation of the organ or tissue for brevity.

In some embodiments, a mismatch between PET image(s) and MR image(s) acquired during PET-MRI imaging (e.g., cardiac imaging) may be improved to some extent by using an integrated PET-MR system that can perform PET imaging and MR imaging concurrently. However, the respiratory motion and/or cardiac motion may still cause a mismatch between the PET image(s) and the MR image(s), which may result in poor image quality of the fusion image(s) of the PET image(s) and the MR image(s). In some embodiments, the respiratory motion may be considered to be the main cause of the mismatch, and the cardiac motion may be a secondary cause of the mismatch, as the frequency of the cardiac motion is higher than the frequency of the respiratory motion. Similar mismatch also occurs between single photon emission computed tomography (SPECT) image(s) and MR image(s). PET, SPECT, or the like may also be referred to as an emission computed imaging (ECT). Thus, it is desirable to provide systems and methods for hybrid imaging that can processing multi-modality images, which can improve the image quality of a fused image of the multi-modality images (e.g., a PET image and an MR image, or a SPECT image and an MR image). As used herein, the hybrid imaging refers to the fusion of two (or more) imaging modalities (e.g., the PET imaging and the MRI imaging, or a SPECT imaging and the MRI imaging) into a single (e.g., a PET-MRI imaging or a SPECT-MRI imaging).

An aspect of the present disclosure relates to a system and method for image fusion. The system and method may obtain a first MR image of a target object (e.g., the heart, a lung, the liver, etc., of the target object). Scan data corresponding to the first MR image may be acquired by an MRI device using a first imaging sequence (e.g., during a breath-hold period of the target object). The system and method may obtain a second MR image of the target object. Scan data corresponding to the second MR image may be acquired by the MRI device using a second imaging sequence. The system and method may obtain a target ECT image of the target object. Scan data corresponding to the target ECT image may be acquired when the target object is breathing freely. The second MR image and the target ECT image may correspond to a target respiratory phase (e.g., an end-expiratory phase of a respiratory cycle). As used herein, when a mismatch between a first image with a first modality (e.g., an MRI image) and a second image with a second modality (e.g., an ECT image) is considered to be caused by something other than an inconsistent between a first respiratory phase corresponding to the first image and a second respiratory phase corresponding to the second image, the first respiratory phase may be designated to match the second respiratory, i.e., the first image and the second image may be designated to correspond to a same respiratory phase. The system and method may fuse the first MR image and the target ECT image based on the second MR image.

According to some embodiments of the present disclosure, for the target ECT image being a target PET image, scan data corresponding to the second MR image and the target PET image may both be acquired when the target object is breathing freely. Scan data corresponding to the second MR image may be acquired using the respiratory gating. The target PET image may be generated using a respiratory gated reconstruction algorithm (e.g., the retrospective respiratory gating). Accordingly, the second MR image can be registered with the target PET image based on the target respiratory phase, which can eliminate or reduce the influence of the respiratory motion on registration. In some embodiments, the second imaging sequence may include a high-resolution imaging sequence (e.g., an imaging sequence for fat-water separation), such that the second MR image can provide clear structural information of the target object. As the first MR image also provides structural information about the target object, the second MR image can be registered with the first MR image based on structural information contained therein, which can eliminate or reduce the influence of the respiratory motion and the cardiac motion on the registration. Thus, the second MR image can act as a bridge for registering the first MR image and the target PET image, thereby registering the first MR image and the target PET image more accurately, which in turn may improve the image quality of the fusion image of the first MR image and the target PET image. In addition, the second MR image may be used to generate an attenuation map for attenuation correction of PET data corresponding to the target PET image, thereby improving the accuracy of the target PET image and the accuracy of the fusion image of the target PET image and the first MR image, which in turn may improve a diagnostic accuracy (e.g., of non-ischemic cardiomyopathies) based on the fusion image.

Figure 1:
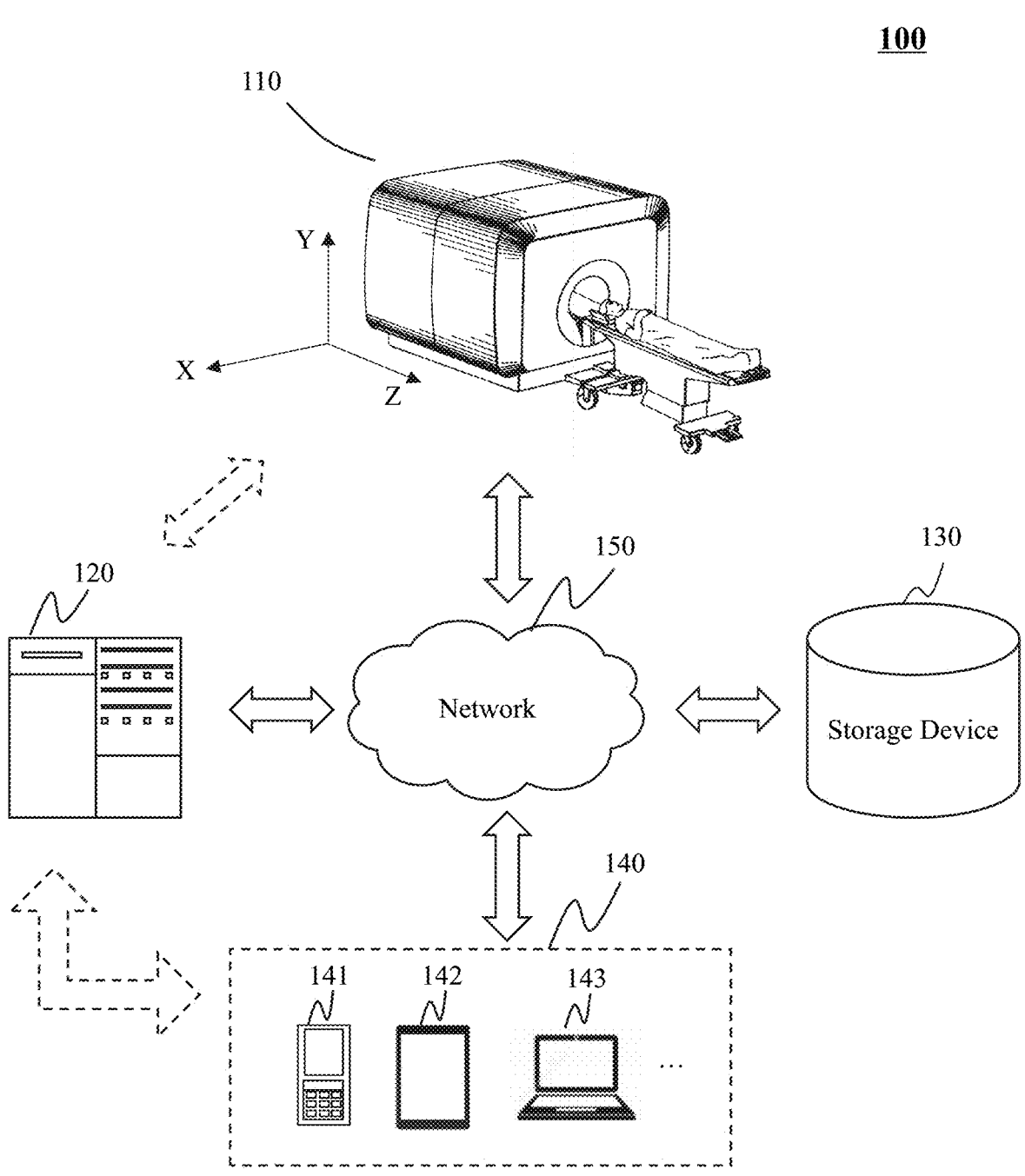
FIG. 1 is a schematic diagram illustrating an exemplary medical system according to some embodiments of the present disclosure.

FIG. 1 is a schematic diagram illustrating an exemplary medical system according to some embodiments of the present disclosure. The medical system 100 may be for non-invasive imaging and/or treatment, such as for disease diagnosis, treatment, and/or research purposes. In some embodiments, the medical system 100 may include a multi-modality system (e.g., a multi-modality imaging system). The term "modality" used herein broadly refers to an imaging or treatment method or technology that gathers, generates, processes, and/or analyzes imaging information of a subject or perform treatment on the subject. For example, the medical system may include an imaging system, e.g., an emission computed tomography (ECT) device such as a positron emission tomography-magnetic resonance imaging (PET-MRI) system.

As illustrated, the medical system 100 may include an imaging device 110, a processing device 120, a storage device 130, a terminal device 140, and a network 150. The components of the medical system 100 may be connected in one or more of various ways. Merely by way of example, as illustrated in FIG. 1, the imaging device 110 may be operably connected to the processing device 120 directly or through the network 150. As another example, the storage device 130 may be operably connected to the imaging device 110 directly or through the network 150. As still another example, the terminal device 140 may be operably connected to the processing device 120 directly or through the network 150.

In some embodiments, the imaging device 110 may be configured to scan at least a part of a subject and acquire image data (or scan data) relating to the subject. The image data may include PET image data, MR image data, etc. The subject may be biological or non-biological. For example, the subject may include a patient, a man-made object, etc. As another example, the subject may include a specific portion, organ, and/or tissue of the patient. For example, the subject may include the heart, a lung, the liver, or the like, or a combination thereof, of the patient. In the present disclosure, the terms "object" and "subject" may be used interchangeably.

In some embodiments, the imaging device 110 may be a PET-MRI device including a PET component (also referred to as a PET device) and an MRI component (also referred to as an MRI device). For example, the PET-MRI device may be a tandem design with the PET component and the MRI component mounted back-to-back, in which both modalities are used sequentially end-to-end on two distinct scanners as part of a single examination. That is, the PET component and MRI component may be in the same room. As another example, the PET-MRI device may be a tandem design with the PET component and the MRI component mounted in different rooms, in which both modalities are used sequentially end-to-end on two distinct scanners as part of a single examination. That is, the PET component and MRI component may share the same table on which the subject is placed for transporting and imaging the subject. As still another example, the PET-MRI device may be an insert design in which the PET component may be removably inserted between radiofrequency coils and gradient coils of the MRI component. As still another example, the PET-MRI device may be a fully integrated design with the PET component and the MRI component mounted on a same gantry, which can perform PET imaging and MRI imaging concurrently. In some embodiments, the imaging device 110 may include additional components such as a camera for positioning the subject before or during imaging. It should be noted that the PET-MRI device, as well as exemplary configurations described herein, is described merely for illustration purposes and not intended to be limiting. The imaging device 110 may include another combination of modalities. Merely by way of example, the imaging device 110 may be a single photon emission computed tomography-magnetic resonance imaging (SPECT-MRI) device including a SPECT component and an MRI component.

The processing device 120 may process data and/or information obtained from the imaging device 110, the storage device 130, and/or the terminal device(s) 140. For example, the processing device 120 may obtain an image (e.g., an MR image or an ECT image such as a PET image) of a target object (e.g., by reconstructing the image based on raw data of the target object). As another example, the processing device 120 may obtain a motion signal (e.g., a respiratory signal) of the subject. As another example, the processing device 120 may register images with the same modality or different modalities. As still another example, the processing device 120 may fuse images with different modalities (e.g., fuse a PET image and an MR image). In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal device(s) 140 via the network 150. As another example, the processing device 120 may be directly connected to the imaging device 110, the terminal device(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal device 140. In some embodiments, the processing device 120 may be part of the imaging device 110.

The storage device 130 may store data, instructions, and/or any other information. In some embodiments, the storage device 130 may store data obtained from the imaging device 110, the processing device 120, and/or the terminal device(s) 140. The data may include image data acquired by the processing device 120, algorithms and/or models for processing the image data, etc. For example, the storage device 130 may store PET data of a subject obtained from a PET device (e.g., the imaging device 110). As another example, the storage device 130 may store a motion signal determined by the processing device 120. As still another example, the storage device 130 may store a fusion image determined by the processing device 120. In some embodiments, the storage device 130 may store data and/or instructions that the processing device 120 and/or the terminal device 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be operably connected to the network 150 to communicate with one or more other components in the medical system 100 (e.g., the processing device 120, the terminal device(s) 140). One or more components in the medical system 100 may access the data or instructions stored in the storage device 130 via the network 150. In some embodiments, the storage device 130 may be integrated into the imaging device 110.

The terminal device(s) 140 may be operably connected to and/or communicate with the imaging device 110, the processing device 120, and/or the storage device 130. In some embodiments, the terminal device 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal device 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the imaging device 110, the processing device 120, the storage device 130, the terminal device(s) 140, etc.) may communicate information and/or data with one or more other components of the medical system 100 via the network 150. For example, the processing device 120 and/or the terminal device 140 may obtain PET data from the imaging device 110 via the network 150. As another example, the processing device 120 and/or the terminal device 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be operably connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart from the scope of the present disclosure. In some embodiments, the medical system 100 may include an image-guided radiotherapy device. For example, the medical system 100 may include an MRI-guided radiotherapy device and an ECT device (e.g., a PET device).

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process imaging data obtained from the imaging device 110, the terminal device(s) 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus, operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage device 220 may store data/information obtained from the imaging device 110, the terminal device (s) 140, the storage device 130, and/or any other component of the medical system 100. The storage device 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the imaging device 110, the terminal device(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
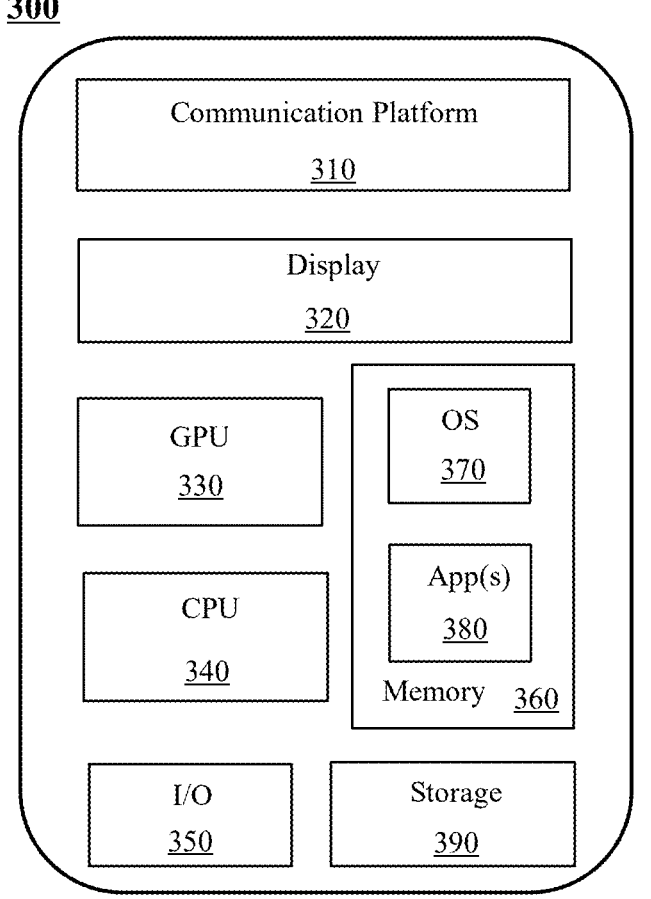
FIG. 3 is a schematic diagram illustrating exemplary hardware and/or software components of an exemplary mobile device on which the terminal device(s) may be implemented according to some embodiments of the present disclosure.

FIG. 3 is a schematic diagram illustrating exemplary hardware and/or software components of an exemplary mobile device 300 on which the terminal device(s) 140 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the medical system 100, and enable data and/or signal to be transmitted between the mobile device 300 and other components of the medical system 100. For example, the communication platform 310 may establish a wireless connection between the mobile device 300 and the imaging device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the medical system 100. For example, the communication platform 310 may transmit data and/or signals inputted by a user to other components of the medical system 100. The inputted data and/or signals may include a user instruction. As another example, the communication platform 310 may receive data and/or signals transmitted from the processing device 120. The received data and/or signals may include imaging data acquired by a detector of the imaging device 110.

In some embodiments, a mobile operating system (OS) 370 (e.g., iOS™ Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information respect to motion signal recalibration or other information from the processing device 120. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
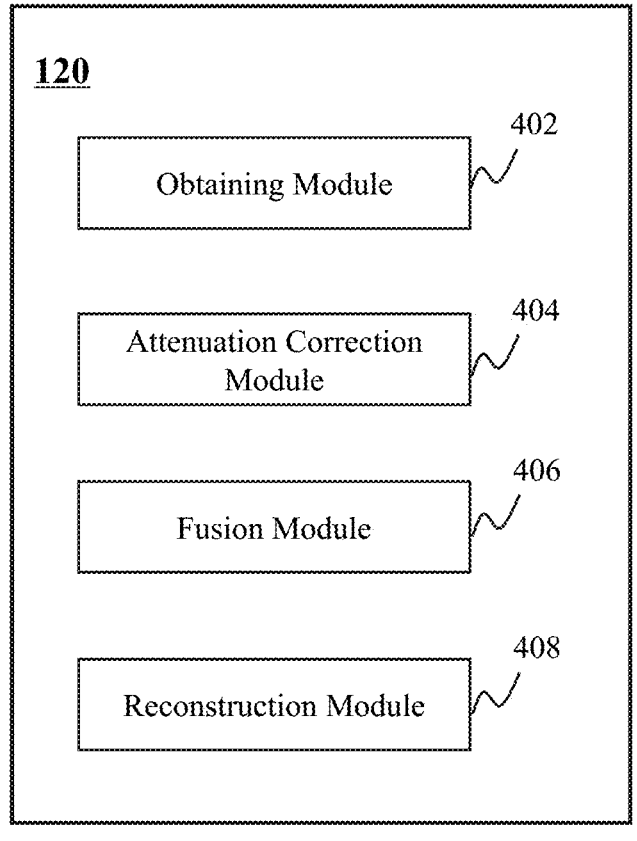
FIG. 4 is a schematic diagram illustrating an exemplary processing device according to some embodiments of the present disclosure.

FIG. 4 is a schematic diagram illustrating an exemplary processing device according to some embodiments of the present disclosure. In some embodiments, the processing device 120 may include an obtaining module 402, an attenuation correction module 404, a fusion module 406, and a reconstruction module 408. The modules may be hardware circuits of at least part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application or set of instructions.

The obtaining module 402 may be configured to obtain information/data from one or more components of the medical system 100. In some embodiments, the obtaining module 402 may obtain image data of a target object from the imaging device 110 or a storage device of the medical system 100. For example, the obtaining module 402 may obtain a first MR image of the target object that is acquired using a first imaging sequence (e.g., a cardiac imaging sequence) when the target object holds his/her breath. As another example, the obtaining module 402 may obtain a second MR image of the target object that is acquired using a second imaging sequence (e.g., an imaging sequence for fat-water separation) when the target object is breathing freely. As still another example, the obtaining module 402 may obtain ECT data (e.g., PET data) of the target object that is acquired when the target object is breathing freely. More descriptions regarding the obtaining of image data of the target object may be found elsewhere in the present disclosure (e.g., FIGS. 5 and 6 and relevant descriptions thereof).

The attenuation correction module 404 may be configured to perform attenuation correction on the ECT data (e.g., the PET data) of the target object. For example, the attenuation correction module 404 may obtain an attenuation map that is determined based on the second MR image of the target object. Alternatively, the attenuation correction module 404 may generate the attenuation map based on the second MR image of the target object. As another example, the attenuation correction module 404 may correct the ECT data (e.g., the PET data) of the target object based on the attenuation map. As still another example, the attenuation correction module 404 may determine a target ECT image (e.g., a target PET image) of the target object. More descriptions regarding the attenuation correction and the determination of the target ECT image may be found elsewhere in the present disclosure (e.g., FIGS. 5 and 6 and relevant descriptions thereof).

The fusion module 406 may be configured to perform image fusion. In some embodiments, the fusion module 406 may fuse the first MR image and the target ECT image based on the second MR image. For example, the fusion module 406 may determine a set of registration parameters by registering the first MR image and the second MR image. The fusion module 406 may fuse the first MR image and the target ECT image based on the set of registration parameters. More descriptions regarding the image fusion may be found elsewhere in the present disclosure (e.g., FIGS. 5 and 6 and relevant descriptions thereof).

The reconstruction module 408 may be configured to perform image reconstruction. For example, the reconstruction module 408 may generate the first MR image based on first scan data of the target object. As another example, the reconstruction module 408 may generate the second MR image based on second scan data of the target object. As still another example, the reconstruction module 408 may generate an ECT image (e.g., the target PET image) based on the ECT data of the target object. More descriptions regarding the image reconstruction may be found elsewhere in the present disclosure (e.g., FIGS. 5 and 6 and relevant descriptions thereof).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the obtaining module 402 and the reconstruction module 408 may be combined into a single module. In some embodiments, one or more modules may be added or omitted in the processing device 120. For example, the processing device 120 may further include a storage module (not shown in FIG. 4) configured to store data and/or information (e.g., the corrected PET image, the fusion image, etc.) associated with the medical system 100. In some embodiments, a module of the processing device 120 may be divided into multiple units. For example, the fusion module 406 may be divided into a first registration unit, a second registration unit, and a fusion unit. The first registration unit may be configured to determine the target ECT image (e.g., the target PET image) corresponding to the second MR image. The second registration unit may be configured to register the first MR image and the second MR image. The fusion unit may be configured to fuse the target ECT image and the first MR image.

FIG. 5 is a flowchart illustrating an exemplary process for image fusion according to some embodiments of the present disclosure. In some embodiments, the process 500 may be implemented in the medical system 100 illustrated in FIG. 1. For example, the process 500 may be stored in the storage device 130 and/or the storage (e.g., the storage device 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3, and/or the modules illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 402, or the reconstruction module 408) may obtain a first MR image of a target object.

In some embodiments, the target object may include the heart, a lung, the liver, etc. of a patient. The target object may undergo a physiological motion (e.g., a respiratory motion and/or a cardiac motion) during imaging (e.g., PET imaging and/or MRI imaging). For example, the target object may hold his/her breath or breath freely during imaging.

In some embodiments, first scan data corresponding to the first MR image may be acquired by an MRI device (e.g., the MR component of the imaging device 110) using a first imaging sequence (also referred to as a first pulse sequence). Taking the heart of the patient as an example, the first imaging sequence may include an fse dark blood sequence, a cine sequence, a perfusion sequence, a late gadolinium enhancement (LGE) sequence, a mapping sequence, a flow sequence, or the like, or any combination thereof. In some embodiments, the first scan data may be acquired with cardiac gating during a breath-hold period of the target object. For example, the target object may hold his/her breath and an electrocardiograph (ECG) gating may be used to control (e.g., trigger) the first imaging sequence for imaging the target object. That is, the first scan data may be acquired by an ECG-gated acquisition during the breath-hold period of the target object. In some embodiments, the first MR image generated based on the first scan data may include a 2D image or a 3D image (including multiple image slices).

In some embodiments, the processing device 120 may obtain the first MR image directly from one or more storage devices (e.g., the storage device 130, the storage device 220, or the storage device 390) of the medical system 100. As another example, the processing device 120 may obtain first scan data of the target object acquired using the first imaging sequence. The processing device 120 may reconstruct the first MR image based on the first scan data of the target object.

In 520, the processing device 120 (e.g., the obtaining module 402 or the reconstruction module 408) may obtain a second MR image of the target object.

In some embodiments, second scan data corresponding to the second MR image may be acquired by the MRI device (e.g., the MRI component of the imaging device 110) using a second imaging sequence (also referred to as a second pulse sequence). The second imaging sequence may be different from the first imaging sequence. For example, the second MR image generated based on the second scan data acquired using the second imaging sequence may be of a higher resolution than the first MR image generated based on the first scan data acquired using the first imaging sequence. That is, structural information in the second MR image may be clearer than structural information in the first MR image. As another example, the second imaging sequence may be performed when the target object is breathing freely, while the first imaging sequence may be performed when the target object holds his/her breath. In some embodiments, the second imaging sequence maybe used for fat-water separation. For example, the second imaging sequence may be related to a two-point Dixon technique, an iterative decomposition of water and fat with echo asymmetric and least-squares estimation (IDEAL) technique, etc. For instance, the second imaging sequence may include a Quick3d_dixon sequence or a non-Quick3d_dixon sequence.

In some embodiments, second scan data corresponding to the second MR image may be acquired with respiratory gating (e.g., a prospective respiratory gating or a predictive respiratory gating). The prospective (or predictive) respiratory gating may be used to control (e.g., trigger) the application of the second imaging sequence for imaging the target object. The prospective (or predictive) respiratory gating may predict when a specific respiratory phase is about to occur based on historical respiratory amplitude(s) or respiratory phase(s) before the specific respiratory phase. That is, the acquisition of the second scan data may be respiratory gated when the target object is breathing freely. For example, during the imaging of the target object, the target object may undergo one or more respiratory cycles. For each of the one or more respiratory cycles, the second imaging sequence may be controlled to acquire second scan data of the target object at a target respiratory phase of the respiratory cycle. Merely by way of example, the target respiratory phase may include an end-expiratory phase of the respiratory cycle. The second MR image may be generated based on the second scan data of the target object. Accordingly, the second MR image may correspond to the target respiratory phase of the target object. More descriptions regarding why selecting the end-expiratory phase as the target respiratory phase may be found elsewhere in the present disclosure (e.g., FIG. 8 and the relevant description thereof). In some embodiments, the second scan data corresponding to the second image may be acquired when the target object undergoes the target respiratory phase (e.g., the end-expiratory phase of a respiratory cycle). The target respiratory phase may be detected by a respiration monitor operably connected with the target object. In some embodiments, the second image may be generated based on the second scan data with respiratory gating (e.g., a retrospective respiratory gating). The retrospective respiratory gating may reconstruct an image (e.g., an MR image or a PET image) based on real/actual respiratory amplitude(s) or real/actual respiratory phase(s) that are acquired when scan data corresponding to the image is acquired. For example, the second scan data may be acquired using radial sampling without the prospective (or predictive) respiratory gating. The second scan data may be reconstructed using the retrospective respiratory gating for generating the second MR image.

In some embodiments, the second MR image generated based on the second scan data may include a 3D MR image. For example, when the second imaging sequence is a Quick3d_dixon sequence, the second MR image may include a 3D MR image that is directly reconstructed based on the second scan data acquired using the Quick3d_dixon sequence. As another example, when the second imaging sequence is a non-Quick3d_dixon sequence, the second scan data acquired using the non-Quick3d_dixon sequence may be reconstructed to generate multiple 2D images (e.g., image slices). The second MR image may include a 3D MR image including the multiple 2D images or a 3D MR image that is generated based on the multiple 2D images (e.g., by a resampling operation).

In some embodiments, the processing device 120 may directly obtain the second MR image from one or more storage devices (e.g., the storage device 130, the storage device 220, or the storage device 390) of the medical system 100. As another example, the processing device 120 may obtain second scan data of the target object acquired using the second imaging sequence with respiratory gating at one or more target respiratory phases. The processing device 120 may determine k-space data by filling one or more k-space lines in a k-space using the second scan data corresponding to the one or more target respiratory phases. The processing device 120 may reconstruct the second MR image based on the k-space data.

In 530, the processing device 120 (e.g., the obtaining module 402, the attenuation correction module 404, or the reconstruction module 408) may obtain a target ECT image of the target object. The target ECT image may include a target PET image, a SPECT image, etc. For illustration purposes, the target PET image is described in the following description, which is not intended to limit the scope of the present disclosure.

In some embodiments, the target PET image may be acquired using a PET device (e.g., the PET component of the imaging device 110). The PET device for acquiring data corresponding to the target PET image and the MRI device for acquiring data corresponding to the first and second MR images may correspond to a same coordinate system during imaging the target object. As used herein, data (e.g., PET data) or scan data corresponding to an image refers to data that may be used to generate the image by way of, e.g., image reconstruction. The same coordinate system may be a coordinate system related to the target object (also referred to as a target object coordinate system). For example, the PET device and the MRI device may be a tandem design in a room, an inert design, or a fully integrated design. In such cases, the target object coordinate system may be determined based on a coordinate system relating to the MRI device, a coordinate system relating to the PET device, or a coordinate system relating to a 3D camera that is mounted in the room and can position the target object. As another example, the PET device and the MRI device may be a tandem design in two rooms and share the same table. In such cases, the target object coordinate system may be determined based on 3D cameras mounted in the two rooms.

In some embodiments, like the second MR image, the target PET image of the target object may correspond to the target respiratory phase of the target object. In some embodiments, the processing device 120 may obtain PET data of the target object acquired when the target object is breathing freely. The processing device 120 may also obtain an attenuation map determined based on the second MR image of the target object. The processing device 120 may determine the target PET image based on the PET data of the target object and the attenuation map. For example, the processing device 120 may correct the PET data based on the attenuation map. The processing device 120 may determine a plurality of candidate PET images using a respiratory gated reconstruction algorithm (e.g., the retrospective respiratory gating). Each of the plurality of candidate PET images may correspond to a respiratory phase of a respiratory cycle. The processing device 120 may determine the target PET image from the plurality of candidate PET images. As another example, the processing device 120 may determine a set of target PET sub-data from the PET data of the target object. The set of target PET sub-data may correspond to the target respiratory phase. The processing device 120 may generate a set of corrected target PET sub-data by correcting, based on the attenuation map, the set of target PET sub-data. The processing device 120 may generate, based on the set of corrected target PET sub-data, the target PET image of the target object. More descriptions regarding the determination of the target PET image of the target object may be found elsewhere in the present disclosure (e.g., FIG. 6 and relevant description thereof).

In 540, the processing device 120 (e.g., the fusion module 406) may fuse, based on the second MR image, the first MR image and the target ECT image (e.g., the target PET image).

As described above, the second MR image and the target PET image may both correspond to the target respiratory phase. Accordingly, the second MR image may correspond to the target PET image, and the registration between the target PET image and the first MR image can be transformed to the registration between the second MR image and the first MR image. That is, multi-modality image registration may be transformed to single-modality image registration that may be easier and more accurate.

In some embodiments, the processing device 120 may determine a set of registration parameters by registering the first MR image and the second MR image. For example, the registration between the first MR image and the second MR image may include a rigid registration. The set of registration parameters may include a matrix (also referred to as a registration matrix) according to which the second MR image can be mapped to the first MR image. The set of registration parameters may include an offset field, a displacement field, a translation, or the like, or any combination thereof. The processing device 120 may fuse, based on the set of registration parameters, the first MR image and the target PET image. For example, the processing device 120 may obtain, in a three-dimensional space (3D space), translational degrees of freedom, rotational degrees of freedom, and telescopic degrees of freedom of the first MR image. If the first MR image is a 2D image, the first MR image may include 8 degrees of freedom. If the first MR image is a 3D image, the first MR image may include 9 degrees of freedom. The processing device 120 may determine the set of registration parameters by registering, according to the translational degrees of freedom, the rotational degrees of freedom, and the telescopic degrees of the first MR image, the first MR image and the second MR image using, e.g., a generalized pattern search (GPS) algorithm. Further, the processing device 120 may determine a registered target PET image based on the target PET image and the set of registration parameters and generate a fusion image by fusing the first MR image and the registered target PET image.

In some embodiments, during the registration process, for an intermediate set of registration parameters, the processing device 120 may assess a registration effect by determining a degree of similarity between the first MR image and a registered PET image of the target PET image transformed based on an intermediate set of registration parameters or a degree of similarity between the first MR image and a registered MR image of the second MR image transformed based on an intermediate set of registration parameters. In response to determining that the registration effect satisfies a preset condition, the processing device 120 may terminate the registration between the first MR image and the second MR image. In some embodiments, the degree of similarity between the first MR image and the registered PET image of the target image may be measured by mutual information and/or normalized mutual information between the first MR image and the registered PET image. Mutual information may reflect a statistical dependence between two random variables or an amount of information that one variable contains about the other. Mutual information may be normalized by using a quantity (or an indicator) including at least one of a joint entropy, a sum of marginal entropies, etc. to provide normalized mutual information. The greater the mutual information and/or normalized mutual information between the first MR image and the registered PET image is, the more the first MR image is aligned with the registered PET image. For example, the mutual information may be maximized when the first MR image is optimally aligned with the registered PET image. In some embodiments, the degree of similarity between the first MR image and the registered MR image may be measured by a cross-correlation, a sum of squared intensity differences, a ratio of image uniformity, or the like, or any combination thereof, between the first MR image and the registered MR image.

Figure 7:
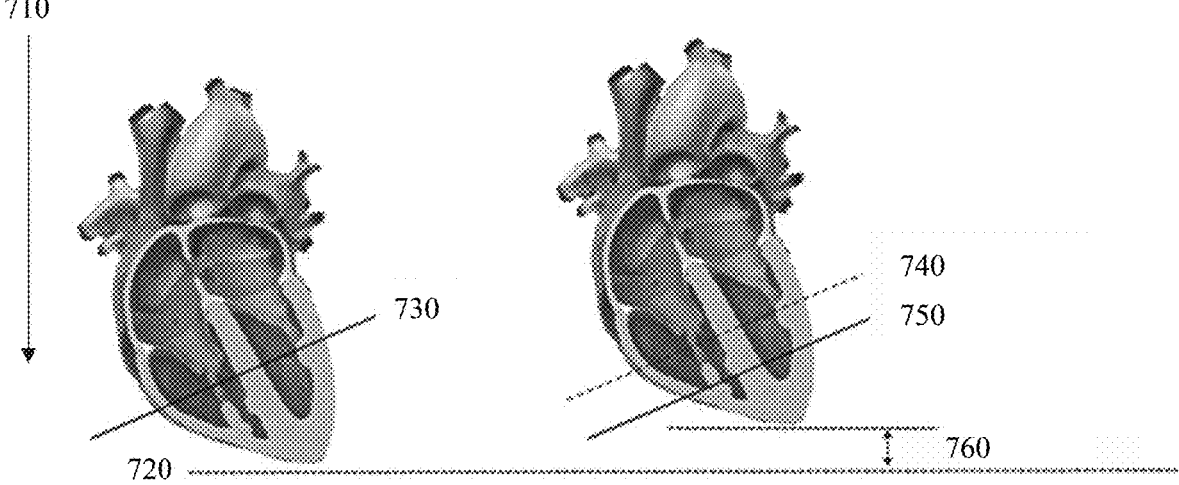
FIG. 7 illustrates an exemplary target object of the heart of a patient according to some embodiments of the present disclosure.

In some embodiments, for the heart of a patient as the target object, the first scan data of the first MR image (e.g., a 2D image) may be acquired along a first plane (e.g., a short axis (SA) plane of the heart); the second scan data of the second MR image may be acquired along a second plane (e.g., a positive plane 720 perpendicular to a superior-inferior direction (e.g., a head-foot direction 710 as shown in FIG. 7) of the patient). The first plane and the second plane may form an angle. The processing device 120 may determine a preliminary second MR image based on the second scan data. The preliminary second MR image may include multiple 2D images (e.g., image slices) parallel to the second plane and arranged along superior-inferior direction. The processing device 120 may determine the second MR image by performing a resampling operation on the preliminary second MR image, such that the second MR image can be registered with the first MR image that is parallel to the first plane. As shown in FIG. 7, a first MR image of the heart of a patient may be acquired along the SA plane 730, and a second MR image may be acquired along the positive plane 720. In some embodiments, due to the respiratory motion 760 of the patient, an expected SA plane 740 and an acquired SA plane 750 corresponding to the first MR image may have a certain displacement. The first MR image corresponding to the expected SA plane 740 and the acquired SA plane 750 may have a mismatch to some extent. Accordingly, before registration of the first MR image and the second MR image, the processing device 120 may process the first MR image by translating, according to a respiratory amplitude of the patient, the first MR image along the head-foot direction 710 of the patient. The processing device 120 may register the translated first MR image and the second MR image. For example, the processing device 120 may determine the translated first MR image by translating the first MR image along the head-foot direction 710 of the patient in a preset displacement range (e.g., [−30 mm, 30 mm]). The translation process may be an iterative optimization with a step length of 1 mm, 2 mm, etc. "−" may indicate that the translated first MR image is closer to the foot of the patient than the first MR image. "+" may indicate that the translated first MR image is closer to the head of the patient than the first MR image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added. For example, an operation for causing the fusion image to be displayed may be added after operation 540. In some embodiments, an operation of the process 500 may be achieved by one or more sub-operations. For example, operation 540 may be divided into a first operation configured to register the first MR image and the second MR image and a second operation configured to fuse the first MR image and the target ECT image (e.g., the target PET image) based on the registration result.

Figure 6:
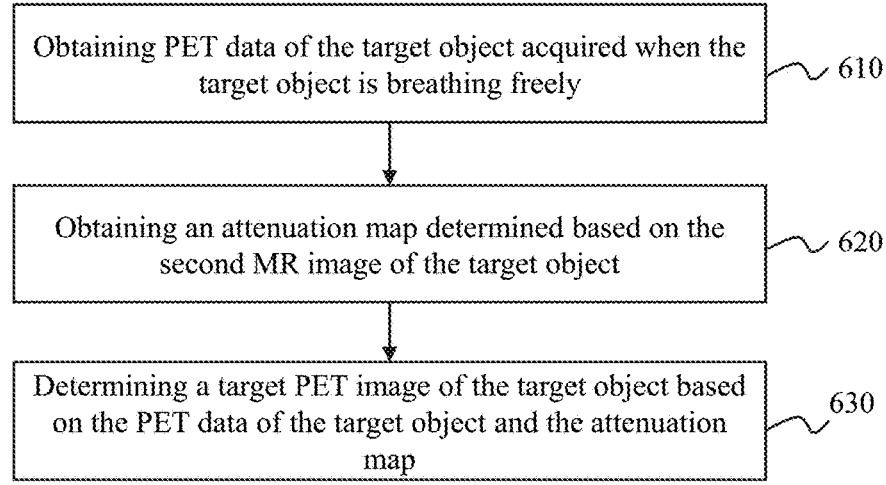
FIG. 6 is a flowchart illustrating an exemplary process for determining a target PET image according to some embodiments of the present disclosure.

FIG. 6 is a flowchart illustrating an exemplary process for determining a target PET image of a target object according to some embodiments of the present disclosure. In some embodiments, the process 600 may be implemented in the medical system 100 illustrated in FIG. 1. For example, process 600 may be stored in the storage device 130 and/or the storage (e.g., the storage device 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 530 in FIG. 5 may be achieved by performing one or more operations of the process 600. In some embodiments, operations 610-630 may be applied to determine another ECT image such as a target SPECT image.

In 610, the processing device 120 (e.g., the obtaining module 402) may obtain PET data of a target object acquired when the target object is breathing freely.

In some embodiments, the PET data of the target object may be in the form of list-mode data or sinogram data. For example, the list-mode data may be projected (e.g., rebinned) to the sinogram data. In some embodiments, during the acquisition of the PET data of the target object, the target object may undergo a respiratory motion of one or more respiratory cycles. Each of the one or more respiratory cycles may correspond to multiple respiratory phases. The multiple respiratory phases may include an intermediate inspiration phase, an end-inspiration phase, an intermediate expiration phase, an end-expiration phase, or the like, or any combination thereof. For example, in the end-inspiration phase, a patient may expand his/her chest to cause a negative pressure in the chest. The negative pressure may cause the air to flow into the lungs of the patient. As another example, in the end-expiration phase, the patient may shrink the chest to cause a positive pressure in the chest. The positive pressure may push the air out of the lungs.

In some embodiments, the processing device 120 may determine the one or more respiratory cycles and/or respiratory phases of each respiratory cycle based on the PET data of the target object and/or detection information of the respiratory motion. For example, the processing device 120 may determine a respiratory signal based on the PET data using a data-driven technique. Exemplary data-driven techniques may include an approach based on a center of mass, an approach based on counts levels, an approach of a principal component analysis (PCA), an approach based on a volume of interest (VOI), or the like, or any combination thereof. The motion signal may be expressed in a two-dimensional coordinate system. The two-dimensional coordinate system may include a first coordinate axis (or the X-axis) representing time, and a second coordinate axis (or the Y-axis) representing amplitude. The respiratory signal may include a plurality of peaks and a plurality of valleys. A respiratory cycle may include a duration between adjacent peaks or a duration between adjacent valleys. As used herein, two peaks of respiratory motion are considered adjacent if there is no other peak of the respiratory motion between the two peaks. As used herein, two valleys of respiratory motion are considered adjacent if there is no other valley of the respiratory motion between the two valleys. A half respiratory cycle may include a duration between a peak and a corresponding valley. As used herein, a peak and a valley of respiratory motion are considered corresponding to each other if there is no other peak or valley of the respiratory motion between the peak and the valley. The processing device 120 may determine the one or more respiratory cycles based on the respiratory signal. As another example, the processing device 120 may obtain the detection information (e.g., respiratory information or a respiratory curve) of the respiratory motion that is concurrently acquired by a respiration detector during the acquisition of the PET data. The detection information may be detected by a resuscitation bag or a corrugated pipe. The processing device 120 may determine the one or more respiratory cycles and the respiratory phases of each respiratory cycle based on the respiratory curve (e.g., amplitudes at various points in the respiratory curve). For instance, a target respiratory phase of the target object in a respiratory cycle may correspond to a continuous range or portion of the respiratory cycle in the respiratory curve.

In 620, the processing device 120 (e.g., the attenuation correction module 404) may obtain an attenuation map (e.g., a μ-map) determined based on a second MR image of the target object.

As described in operation 520, the scan data of the second MR image of the target object may be acquired using the second imaging sequence. In some embodiments, the second imaging sequence may be configured to generate scan data that may be used to generate an MR image with high resolution in comparison with an MR image corresponding to the first imaging sequence. For instance, the second imaging sequence may be an imaging sequence for fat-water separation. In some embodiments, the attenuation map may be previously determined and stored in a storage device (e.g., the storage device 130, the storage device 220, or the storage 390) of the medical system 100. The processing device 120 may directly retrieve the attenuation map from the storage device.

In some embodiments, the processing device 120 may obtain the second MR image and generate the attenuation map based on the second MR image. For example, the processing device 120 may segment the second MR image into different portions (including, e.g., water, fat, air, bones, and lungs) based on a segmentation algorithm, a truncation compensation algorithm, or the like, or any combination thereof. The different portions may correspond to different attenuation coefficients (or attenuation values). For instance, the air may correspond to the minimum attenuation coefficient, and the bones may correspond to the maximum attenuation coefficient. The processing device 120 may determine the attenuation map based on the different attenuation coefficients corresponding to the different portions.

In 630, the processing device 120 (e.g., the attenuation correction module 404, the reconstruction module 408, etc.) may determine a target PET image of the target object based on the PET data of the target object and the attenuation map.

In some embodiments, the processing device 120 may generate corrected PET data by correcting, based on the attenuation map, the PET data of the target object. The processing device 120 may generate, based on the corrected PET data, a plurality of candidate PET images using a respiratory gated reconstruction algorithm (e.g., the retrospective respiratory gating). For example, the processing device 120 may divide, based on respiratory gating, the corrected PET data into a plurality of sections (e.g., PET sub-data) such that one of the plurality of sections may correspond to a respiratory phase of a respiratory cycle of the one or more respiratory cycles. The processing device 120 may process each of the plurality of sections to generate a candidate PET image. Further, the processing device 120 may determine, based on the target respiratory phase, the target PET image of the target object from the plurality of candidate PET images. For example, the processing device 120 may determine a set of candidate PET images from the plurality of candidate PET images based on the target respiratory phase. The set of candidate PET images may correspond to the target respiratory phase. The processing device 120 may determine a target PET image from the set of candidate PET images. The target PET image may be a candidate PET image that best matches with the second MR image among the set of candidate PET images. For instance, the processing device 120 may determine the target PET image from the set of candidate PET images according to an instruction of a user (e.g., a doctor, a technician, or an operator). Alternatively, the processing device 120 may determine the target PET image from the set of candidate PET images automatically. For example, the processing device 120 may register the second MR image with each candidate PET image of the set of candidate PET images to determine a second set of registration parameters. The second set of registration parameters may include a matrix that can align a candidate PET image with the second MR image. The processing device 120 may determine a registered candidate PET image based on the second set of registration parameters and a corresponding candidate PET image. The processing device 120 may determine a degree of similarity between the second MR image and the registered candidate PET image. The degree of similarity between the second MR image and the registered candidate PET image may be measured by mutual information and/or normalized mutual information between the second MR image and the registered candidate PET image. The greater the mutual information and/or normalized mutual information between the second MR image and the registered candidate PET image is, the better the second MR image aligns with the registered candidate PET image. The processing device 120 may determine, based on degrees of similarity corresponding to the set of candidate PET images, a specific candidate PET image among the set of candidate PET images as the target PET image. The specific candidate PET image may correspond to a degree of similarity satisfying a similarity criterion. For example, the similarity criterion may include that the degree of similarity of a specific candidate PET image is maximum among the degree of similarity corresponding to the set of candidate PET images. As another example, the similarity criterion may include that the degree of similarity of the specific candidate PET image is greater than a threshold degree of similarity.

In some embodiments, the processing device 120 may determine a set of target PET sub-data from the PET data of the target object. For example, the processing device 120 may divide, based on respiratory gating, the PET data of the target object into a plurality of sets of PET sub-data such that one set of PET sub-data of the plurality of sets of PET sub-data may correspond to a respiratory phase of a respiratory cycle of the one or more respiratory cycles. The processing device 120 may determine, based on the target respiratory phase and from the plurality of sets of PET sub-data, the set of target PET sub-data that corresponds to the target respiratory phase. The processing device 120 may generate a set of corrected target PET sub-data by correcting, based on the attenuation map, the set of target PET sub-data. The processing device 120 may generate, based on the set of corrected target PET sub-data, the target PET image of the target object. For example, the set of corrected target PET sub-data may correspond to one or more target respiratory phases of different respiratory cycles. The processing device 120 may generate, based on the set of corrected target PET sub-data, one or more candidate PET images each of which corresponds to one of the one or more target respiratory phases. The processing device 120 may determine the target PET image from the one or more candidate PET images according to an instruction of the user or automatically, the same as or similar to the determination of the target PET image from the set of candidate PET images as described above the description which is not repeated here.

By attenuation correction of the PET data using the attenuation map, the target PET image that is generated based on attenuation corrected PET data may be of improved image quality.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may include one or more additional operations or one or more operations may be omitted. For example, the process 600 may include an additional operation for fusing the second MR image and the target PET image. For instance, the processing device 120 may fuse the second MR image and the target PET image based on a second set of registration parameters between the second MR image and the target PET image. By fusing the second MR image and the target PET image, the influence of the respiratory motion on registration may be eliminated or reduced, thereby improving the image quality of the fused PET-MR image of the second MR image and the target PET image. In some embodiments, an operation of the process 600 may be achieved by one or more sub-operations. For example, operation 630 may be achieved by a first sub-operation configured for attenuation correction and a second sub-operation configured for data division according to respiratory phases.

In some embodiments, the processing device 120 may determine the attenuation map based on the second MR image and a target neural network model. The target neural network may provide a mapping between an MR image and an attenuation map corresponding to the MR image. For example, the processing device 120 may input the second MR image into the target neural network model. The processing device 120 may determine the attenuation map based on an output of the target neural network. For example, the target neural network may transform the second MR image to a pseudo CT image. The processing device 120 may segment bones from the pseudo CT image. The processing device 120 may add bone density information in the pseudo CT image to generate the attenuation map. In some embodiments, the target neural network may include a convolutional neural network (CNN) model, a back propagation neural network (BPNN) model, a radial basis function neural network (RBFNN) model, a deep belief network (DBN) model, an Elman neural network model, or the like, or any combination thereof. In some embodiments, the target neural network may be determined based on a plurality of groups of training samples. Each group of the plurality of groups of training samples may include a sample MR image, and an attenuation map corresponding to a sample CT image. The sample MR image and the sample CT image may correspond to a same portion (e.g., the heart, a lung, the liver, the chest, etc.) of a sample object. The attenuation map corresponding to the sample CT image may be determined by: determining different portions (e.g., organs or tissue including lungs, fat, bones (e.g., ribs, the spine, etc.), the heart); and allocating attenuation values for the different portions to generate the attenuation map corresponding to the sample CT image. Alternatively, the attenuation map corresponding to the sample CT image may be determined by determining the different portions (e.g., organs or tissue including lungs, fat, bones (e.g., ribs, the spine, etc.), the heart); registering the sample CT image and a sample PET image corresponding to the same portion as the sample CT image; and allocating attenuation values for the different portions in the registered sample, PET image to generate the attenuation map corresponding to the sample CT image. In some embodiments, the attenuation map corresponding to the sample CT image may be determined by performing a linear transformation on the sample CT image.

FIG. 8 is a schematic diagram illustrating different exemplary imaging manners according to some embodiments of the present disclosure. Imaging manner 1 refers to ECG gated acquisitions using an LGE sequence during breath-hold periods at an end-expiration phase. Imaging manner 2 refers to ECG gated acquisitions using an LGE sequence during breath-hold periods at an end-inspiration phase. Imaging manner 3 refers to respiratory gated acquisitions using a second imaging sequence (e.g., aDixon-GRE_quick3d sequence) during free heart beating periods. Imaging manner 4 refers to a free breathing PET acquisition during free heart beating periods. Imaging manner 5 refers to list-mode PET data acquisition during free heart beating periods and PET images generated using a respiratory gated reconstruction algorithm (e.g., the retrospective respiratory gating). For example, list-mode PET data may be rebinned into respiratory gated sinograms for reconstruction. As shown in FIG. 8, ring images 820, 830, 840, and 850 in light color represent images acquired under imaging manners B-E respectively; ring image 810 in dark color (also referred to as a reference image) represents an image acquired under imaging manner 1. Image 820 acquired under imaging manner 2 has a significant mismatch with the reference image 810, indicating a position (a position of, e.g., the myocardium of the heart) determined based on image 820 acquired under imaging manner does not align with a position determined based on the reference image 810. In actual cardiac imaging, imaging manner 1 may be used for obtaining images of a patient. If the patient does not hold his/her breath during cardiac imaging, images of the patient may be acquired under imaging manner 2, resulting in a significant mismatch between image 820 and the reference image 810. A position (indicating a position of, e.g., the myocardium of the heart) determined based on image 830 acquired under imaging manner 3 aligns with a position determined based on the reference image 810, while a thickness (indicating a thickness of, e.g., the myocardium of the heart) determined based on image 830 may be different from a thickness determined based on the reference image 810. Image 840 acquired under imaging manner 4 shows a mismatch with the reference image 810, indicating a position determined based on image 840 is different from the position determined based on the reference image 810. A position determined based on image 850 (indicating a position of, e.g., the myocardium of the heart) acquired under imaging manner 5 aligns with the position determined based on the reference image 810, while a thickness ((indicating a thickness of, e.g., the myocardium of the heart) determined based on image 850 is different from the thickness determined based on the reference image 810, similar to image 830 acquired under imaging manner 3 compared to the reference image 810. Accordingly, during PET-MRI imaging, imaging manner 3 and imaging manner 5 may be selected for registration/matching.

FIG. 9 is a schematic diagram illustrating an exemplary process for image registration according to some embodiments of the present disclosure. As shown in 910, PET image data (i.e. PET image average as referred to in FIG. 9) of the heart of a patient may be acquired using a PET component of the imaging device 110. The PET image data may be processed using a respiratory gated reconstruction algorithm (e.g., the retrospective respiratory gating) to generate PET images (920-1, 920-2, 920-3, . . . , 920-*n*) corresponding to a plurality of respiratory phases (e.g., phase 1, phase 2, . . . , phase n). An end-expiratory phase may be determined to be the target phase (phase m as referred to in FIG. 9) according to, e.g., a user instruction, a default setting of the system performing the image registration process illustrated in FIG. 9. A PET image 910-*m* (e.g., the target PET image as described elsewhere in the present disclosure) corresponding to the end-expiratory phase (e.g., phase m) may be matched/registered with an MR image 940 (e.g., the second MR image as described elsewhere in the present disclosure) that is acquired using a second imaging sequence (e.g., a Quick3d_dixon sequence) with respiratory gating. The target PET image 910-*m* and the second MR image 940 may both correspond to the target phase. The second MR image may be used as a bridge to obviate the need to directly register the target PET image 920-*m* with an MR image 950 (e.g., an MR image 950-1, 950-2, 950-3, 950-4, 950-5, or 950-6) (e.g., the first MR image as described elsewhere in the present disclosure). The first MR image 950 may be acquired using an imaging sequence (e.g., an fse dark blood sequence, a cine sequence, a perfusion sequence, an LGE sequence, a mapping sequence, a flow sequence, etc.) according to a breath hold and ECG gated acquisition process 960. Instead, the first MR image 940 and the second MR image 950 may be registered to determine a registration matrix. The registration matrix may include motion vector fields between the first MR image and the second MR image. The target PET image 910-*m* may be transformed based on the registration matrix to generate a transformed PET image. An accurate matching between the transformed PET image and the first MR image 950 may be achieved, while the target PET image 910-*m* and the first MR image 950 may have a mismatch. More descriptions regarding the image registration may be found elsewhere in the present disclosure (e.g., FIGS. 5 and 6 and relevant descriptions thereof).

In some embodiments, in hybrid imaging (e.g., multi-modality cardiac imaging), images of different modalities (e.g., a PET image and an MR image, or a SPECT image and an MR image) may need to be registered. When an image with a specific modality (e.g., PET or SPECT) shows a fuzzy cardiac structure or cannot show an anatomical boundary of the cardiac structure, a user usually cannot judge whether the registration between images of two modalities is accurate, letting alone manual or automatic registration. In the present disclosure, by studying processing characteristics of different modalities for respiratory motion and cardiac motion, a rule may be employed in registering images of different modalities that if the respiratory motion and cardiac motion in image acquisition by different modalities are dealt with an approximate or similar strategy, the size and position of the heart may remain consistent in images acquired by the different modalities. According to the rule, an image (e.g., the second MR image) with a clear anatomical structure may be acquired and used, instead of an image (e.g., the target PET image) with an unclear anatomical structure, for registering/matching with the first MR image, which can greatly improve the efficiency of registration. For example, for a PET image associated with inflammation of the myocardium in PET/MRI imaging, only the myocardium at a lesion site may show high uptake in the PET image, while other portions of the myocardium may be unclear in the PET image. Accordingly, there may be a mismatch between the PET image and an MR image acquired during the PET/MRI imaging, which in turn may affect the correction of the PET image after the mismatch. The present disclosure provides a method for using an MR image with a clear anatomical structure that is acquired using an imaging sequence (e.g., the second imaging sequence) used for fat-water separation to bridge a two-stage registration to achieve a registration between the PET image with the MR image acquired using a cardiac imaging sequence (e.g., the first imaging sequence), thus solving the problem (e.g., a mismatch between the PET image and the MR image acquired during the cardiac PET/MRI imaging) that previously is not solved clinically. Specifically, the MR image with a clear anatomical structure that is acquired using a second imaging sequence may be registered with the PET image and also with the MR image acquired using a cardiac imaging sequence to achieve a registration between the PET image and the MR image acquired using the cardiac imaging sequence. As used herein, the two-stage registration refers to a registration process including a first stage of registering the second MR image acquired using the second imaging sequence with the target PET image, and a second stage of registering the second MR image with the first MR image that is acquired using the first imaging sequence, according to which the target PET image and the first MR image can be accurately registered for further fusion.

Figure 10A:
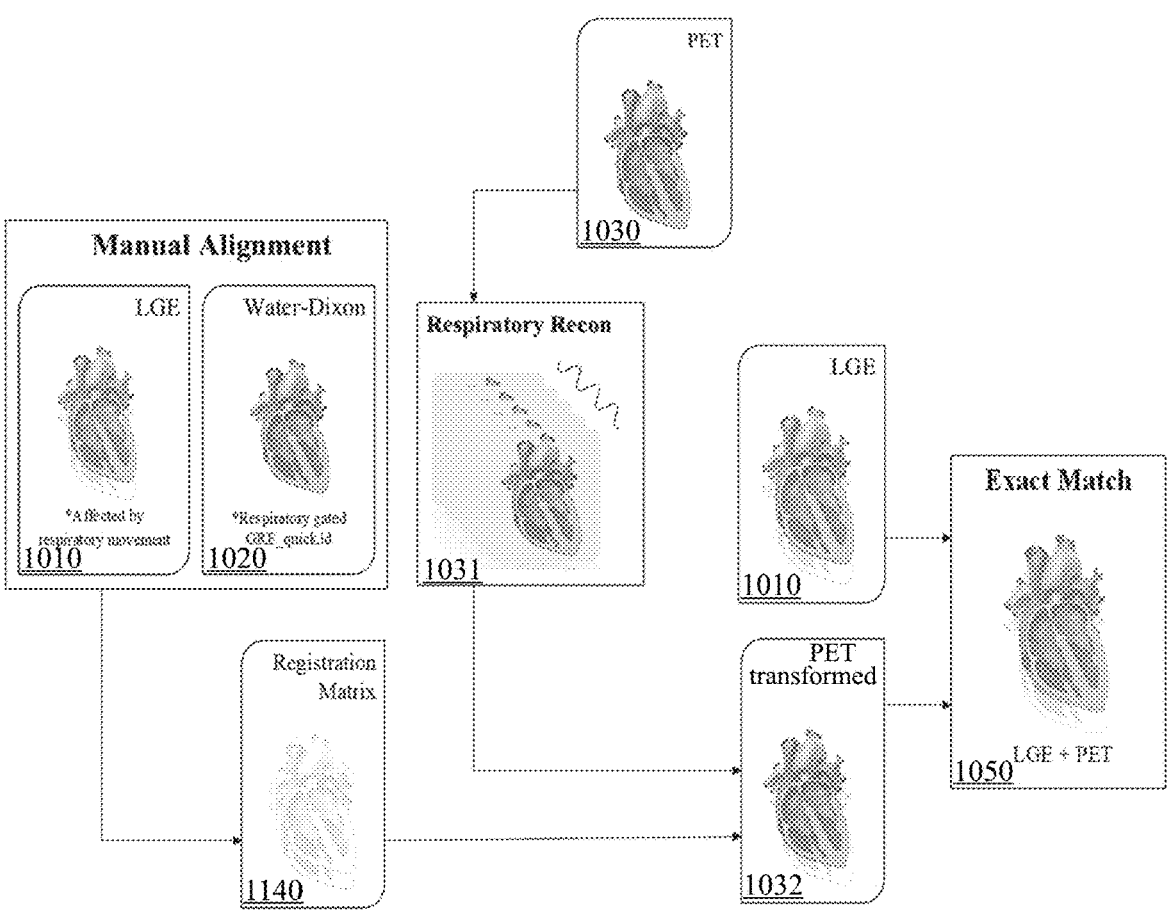
FIGS. 10A and 10B are schematic diagrams illustrating an exemplary process for image fusion according to some embodiments of the present disclosure.
Figure 10B:
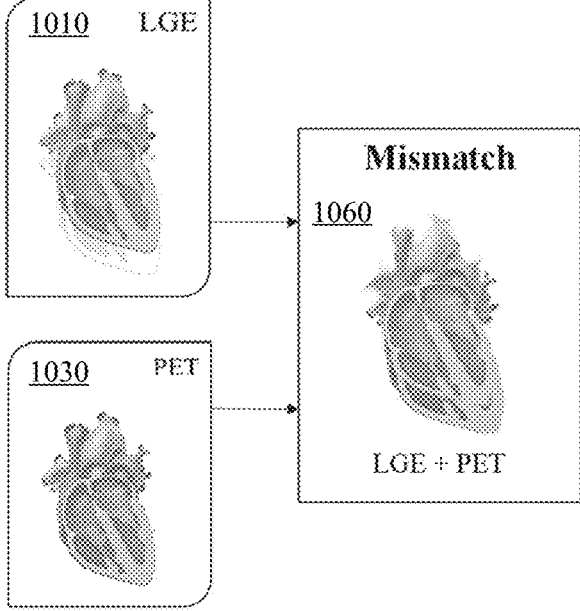

FIGS. 10A and 10B are schematic diagrams illustrating an exemplary process for image fusion according to some embodiments of the present disclosure. As shown in FIG. 10A, image 1010 was a first MR image of the heart of a patient acquired using an LGE sequence, which may be affected by respiratory movement (or motion). Image 1020 was a second MR image acquired using a fat water separation sequence with respiratory gating (e.g., a respiratory gated GRE_quick3d sequence). Image 1010 and image 1020 were registered to determine a registration matrix 1140. Image 1030 was a PET image acquired when the patient was breathing freely. Image 1030 was processed using a respiratory gated reconstruction to generate a plurality of images 1031 corresponding to a plurality of respiratory phases. A target PET image was determined from the plurality of images 1031 and transformed according to the registration matrix 1140 to generate transformed PET image 1032. Image 1010 and the transformed PET image 1032 were fused to generate fusion image 1050. Image 1010 and image 1030 were registered for fusion according to a two-stage image registration. The two-stage image registration includes a first stage of determining image 1020 that best matches image 1020 and a second stage for registering image 1032 and image 1020. As shown in FIG. 10B, image 1010, and image 1030 were fused directly to generate fusion image 1060. Fusion image 1050 had an improved image quality than fusion image 1060, indicating that the two-stage registration achieves an exact match for image fusion while the direct registration has a mismatch for image fusion.

Figure 11:
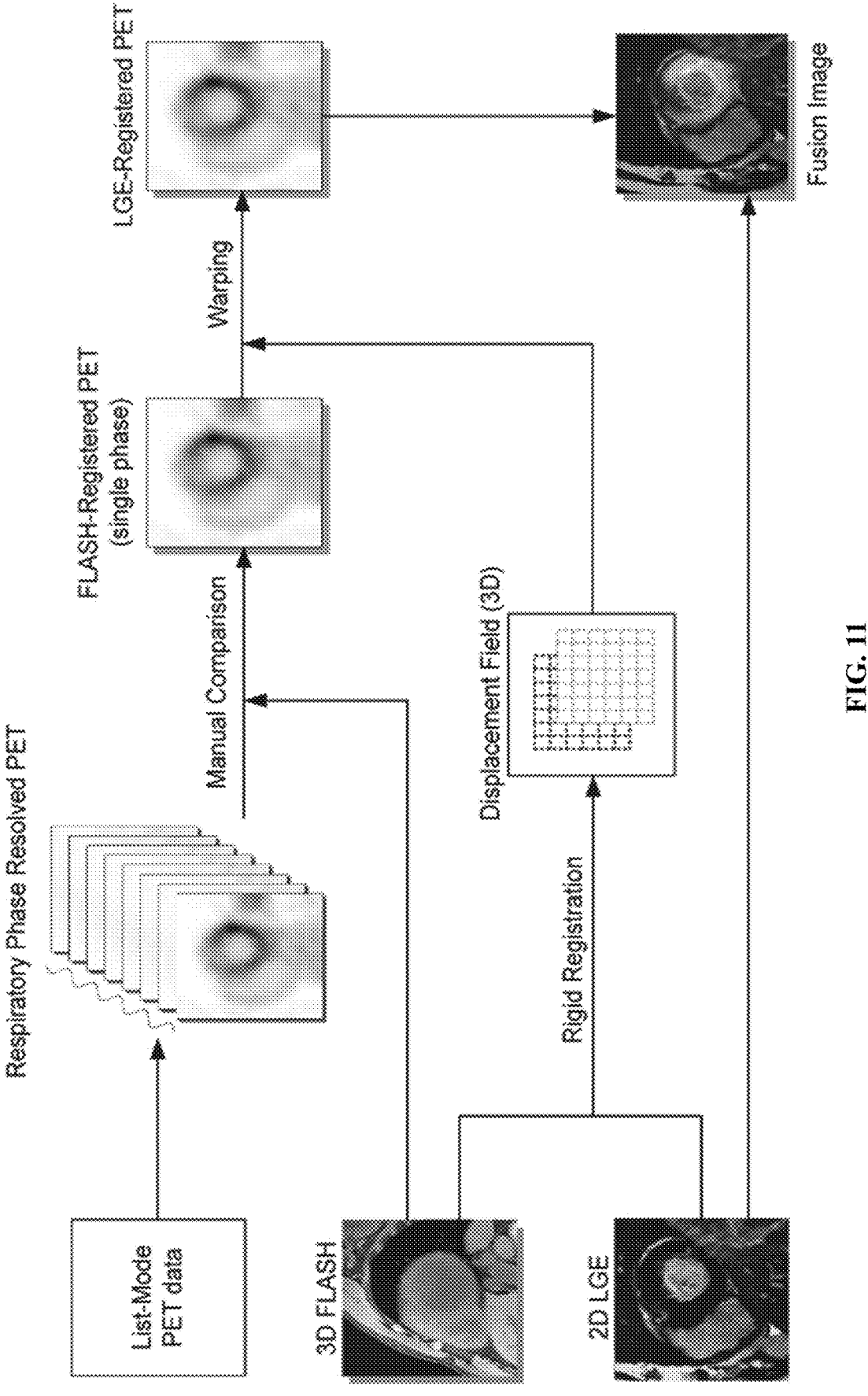
FIG. 11 is a schematic diagram illustrating an exemplary two-stage image registration according to some embodiments of the present disclosure.

FIG. 11 is a schematic diagram illustrating an exemplary two-stage image registration according to some embodiments of the present disclosure. As shown in FIG. 11, the image registration of LGE and PET images was a two-stage registration. Firstly, list-mode PET data was divided (e.g., binned) into eight respiratory sections (e.g., bins) based on a respiratory signal. Secondly, 3D FLASH (e.g., the second MR image) and respiratory phase resolved (RPR) PET images were compared to determine a FLASH-registered phase image (e.g., the target PET image). Thirdly, a rigid registration was manually/automatically performed between 3D FLASH and 2D LGE (e.g., the second MR image and the first MR image to determine a 3D displacement field. Fourthly, the FLASH-registered PET image was warped using the 3D displacement field to generate an LGE-registered PET image. Finally, the LGE-registered PET image and the 2D LGE image were fused to generate a fusion image as shown in FIG. 11.

FIG. 12 illustrates exemplary images according to some embodiments of the present disclosure. As shown in FIG. 12, image A was a short-axial LGE image (an MR image of scan data acquired using an LGE sequence) of a patient with DCM who was undergoing fasting, image B was an LGE and PET fusion image before registration, and image C was an LGE and PET fusion image after two-stage registration. Image B shows a significant mismatch between LGE and PET images (e.g., where the arrow points), while a displacement between LGE and PET images in image C can hardly be detected.

FIG. 13 is a flowchart illustrating an exemplary process for image fusion according to some embodiments of the present disclosure. In some embodiments, the process 1300 may be implemented in the medical system 100 illustrated in FIG. 1. For example, the process 1300 may be stored in the storage device 130 and/or the storage (e.g., the storage device 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3, and/or the modules illustrated in FIG. 4). The operations of the illustrated process presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1310, the processing device 120 (e.g., the obtaining module 402) may obtain a first image of a target object and a second image of the target object. The first image and the second image may correspond to a first modality.

In some embodiments, the first modality may be MRI. For example, the first image may be a first MR image that is acquired by an MRI device using a first imaging sequence during a breath-hold period of the target object. More descriptions regarding the first MR image may be found elsewhere in the present disclosure (e.g., operation 510 and relevant descriptions thereof). The second image may be a second MR image that is acquired by the MRI device using a second imaging device when the target object is breathing freely. The second image may correspond to a target respiratory phase of the target object. More descriptions regarding the second MR image may be found elsewhere in the present disclosure (e.g., operation 520 and relevant descriptions thereof).

In 1320, the processing device 120 (e.g., the obtaining module 402, the attenuation correction module 404, or the reconstruction module 408) may determine a target image based on the second image of the target object. The target image may correspond to a second modality.

In some embodiments, the second modality may be ECT (e.g., PET or SPECT). The target image may be a target ECT image (e.g., a target PET image or a target SPECT image). In some embodiments, the processing device 120 may obtain ECT data of the target object acquired when the target object is breathing freely. The processing device 120 may obtain an attenuation map determined based on the second image of the target object. The processing device 120 may determine the target ECT image of the target object based on the ECT data of the target object and the attenuation map. More descriptions regarding the target ECT image and the determination thereof may be found elsewhere in the present disclosure (e.g., operation 530, FIG. 6 and relevant descriptions thereof).

In 1330, the processing device 120 (e.g., the fusion module 406) may determine a set of registration parameters by registering the first image and the second image.

In some embodiments, the registration between the first image and the second image may include a rigid registration. The set of registration parameters may include a matrix (also referred to as a registration matrix) according to which the second image can be mapped to the first image. More descriptions regarding the determination of the set of registration parameters may be found elsewhere in the present disclosure (e.g., operation 540 and the relevant decryptions thereof).

In 1340, the processing device 120 (e.g., the fusion module 406) may fuse the first image and the target image based on the set of registration parameters In some embodiments, the processing device 120 may determine a registered target image based on the target image and the set of registration parameters. The processing device 120 may generate the fusion image by fusing the first image and the registered target image. More descriptions regarding the fusion process may be found elsewhere in the present disclosure (e.g., operation 540 and the relevant descriptions thereof).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for hybrid imaging, comprising:
at least one non-transitory storage device including a set of instructions; and
at least one processor configured to communicate with the at least one non-transitory storage device, wherein when executing the set of instructions, the at least one processor is configured to direct the system to perform operations including:
obtaining a first magnetic resonance (MR) image of a target object, the first MR image being acquired by a magnetic resonance imaging (MRI) device using a first imaging sequence with cardiac gating during a breath-hold period of the target object;
obtaining a second MR image of the target object, the second MR image being acquired with respiratory gating, by the MRI device using a second imaging sequence, when the target object is breathing freely;
obtaining emission computed tomography (ECT) data of the target object acquired when the target object is breathing freely;
generating, based on the ECT data, candidate ECT images corresponding to a plurality of respiratory phases using a respiratory gated reconstruction algorithm;
determining a target ECT image matching the second MR image from the candidate ECT images corresponding to the plurality of respiratory phases;
determining a set of registration parameters between the first MR image and the second MR image by registering the first MR image and the second MR image;
transforming the target ECT image based on the set of registration parameters; and
generating an ECT-MR fusion image by fusing the first MR image and the transformed target ECT image.

2. The system of claim 1, wherein the target respiratory phase includes an end-expiratory phase of a respiratory cycle.

3. The system of claim 1, wherein the second MR image is acquired or reconstructed with respiratory gating.

4. The system of claim 1, wherein the second MR image and the target ECT image correspond to a same coordinate system.

5. The system of claim 1, wherein the generating, based on the ECT data, candidate ECT images corresponding to a plurality of respiratory phases using a respiratory gated reconstruction algorithm includes:

obtaining an attenuation map determined based on the second MR image of the target object;

generating corrected ECT data by correcting, based on the attenuation map, the ECT data of the target object; and generating, based on the corrected ECT data, a plurality of candidate ECT images, each of the plurality of candidate ECT images corresponding to a respiratory phase of a respiratory cycle.

6. The system of claim 5, wherein the obtaining the attenuation map determined based on the second MR image of the target object includes:

inputting the second MR image into a target neural network model;

transforming the second MR image to a pseudo CT image based on the target neural network model;

segmenting bones from the pseudo CT image based on the target neural network model; and adding bone density information in the pseudo CT image to generate the attenuation map.

7. The system of claim 1, wherein the determining the set of registration parameters includes:

obtaining, in a three-dimensional space, translational degrees of freedom, rotational degrees of freedom, and telescopic degrees of freedom of the first MR image; and determining the set of registration parameters by registering, according to the translational degrees of freedom, the rotational degrees of freedom, and the telescopic degrees, the first MR image and the second MR image using a generalized pattern search (GPS) algorithm.

8. The system of claim 1, wherein the first imaging sequence includes at least one of a fse dark blood sequence, a cine sequence, a perfusion sequence, a late gadolinium enhancement (LGE) sequence, a mapping sequence, or a low sequence.

9. The system of claim 1, wherein the second imaging sequence is related to a two-point Dixon technique or an iterative decomposition of water and fat with echo asymmetric and least-squares estimation technique.

10. The system of claim 1, wherein the first MR image includes a 2D image or a 3D image, and the second MR image includes a 3D image.

11. The system of claim 1, wherein the second MR image obtained using the second imaging sequence is of a higher resolution than the first MR image obtained using the first imaging sequence.

12. The system of claim 1, wherein the first MR image is a 2D image generated based on first scan data, the first scan data being acquired along a first plane, the second MR image is a 3D image generated based on second scan data, the second scan data being acquired along a second plane, and the first plane and the second plane form an angle.

13. The system of claim 12, wherein the second MR image is generated by:

generating a preliminary second MR image based on the second scan data, the preliminary second MR image including multiple 2D images parallel to the second plane; and determining the second MR image by performing a resampling operation on the preliminary second MR image.

14. The system of claim 12, wherein the determining a set of registration parameters between the first MR image and the second MR image by registering the first MR image and the second MR image comprises:

obtaining a translated first MR image by translating the first MR image along a head-foot direction of the target object according to a respiratory amplitude of the target object; and determining the set of registration parameters by registering the translated first MR image and the second MR image.

15. The system of claim 1, wherein the target ECT image is not involved in a determination process of the set of registration parameters.

16. The system of claim 1, wherein the determining a target ECT image matching the second MR image from the candidate ECT images corresponding to the plurality of respiratory phases including:

for each of the candidate PET images, registering the candidate PET image with the second MR image to generate a corresponding registered candidate PET image; and determining a similarity degree between the second MR image and the registered candidate ECT image; and determining, from the candidate ECT images corresponding to the plurality of respiratory phases, a candidate ECT image corresponding to the maximum similarity degree as the target ECT image.

17. A method for hybrid imaging, which is implemented on a computing device that includes at least a non-transitory storage device and at least the processor, the method comprising:

obtaining a first magnetic resonance (MR) image of a target object, the first MR image being acquired by a magnetic resonance imaging (MRI) device using a first imaging sequence;

obtaining a second MR image of the target object, the second MR image being acquired by the MRI device using a second imaging sequence with respiratory gating, and the second MR image corresponding to a target respiratory phase of the target object;

obtaining emission computed tomography (ECT) data of the target object when the target object is breathing freely;

generating, based on the ECT data, candidate ECT images corresponding to a plurality of respiratory phases using a respiratory gated reconstruction algorithm;

determining a target ECT image matching the second MR image from the candidate ECT images corresponding to the plurality of respiratory phases;

determining a set of registration parameters between the first MR image and the second MR image by registering the first MR image and the second MR image; and generating an ECT-MR fusion image by fusing, based on the set of registration parameters between the first MR image and the second MR image, the first MR image and the target ECT image, wherein a registration between the target ECT image and the first MR image is transformed to the registration between the second MR image and the first MR image.

18. A system for hybrid imaging, comprising:

at least one non-transitory storage device including a set of instructions; and at least one processor configured to communicate with the at least one non-transitory storage device, wherein when executing the set of instructions, the at least one processor is configured to direct the system to perform operations including:

obtaining a first magnetic resonance (MR) image of a target object, the first MR image being acquired by a magnetic resonance imaging (MRI) device using a first imaging sequence;

obtaining a second MR image of the target object, the second MR image being acquired by the MRI device using a second imaging sequence with respiratory gating, and the second MR image corresponding to a target respiratory phase of the target object;

obtaining emission computed tomography (ECT) data of the target object when the target object is breathing freely;

generating, based on the ECT data, candidate ECT images corresponding to a plurality of respiratory phases using a respiratory gated reconstruction algorithm;

determining a target ECT image matching the second MR image from the candidate ECT images corresponding to the plurality of respiratory phases;

determining a set of registration parameters between the target ECT image and the first MR image by registering the first MR image and the second MR image, wherein the target ECT image is not involved in a determination process of the set of registration parameters, and generating an ECT-MR fusion image by fusing, based on the set of registration parameters, the first MR image and the target ECT image.

\* \* \* \* \*